(12) United States Patent
Paik et al.

(10) Patent No.: US 10,526,218 B2
(45) Date of Patent: Jan. 7, 2020

(54) FLOW CONTROL METHOD AND APPARATUSES

(71) Applicant: The Board of Trustees of the Leland Stanford Junior University, Palo Alto, CA (US)

(72) Inventors: Kee-Hyun Paik, Santa Clara, CA (US); Yang Liu, San Jose, CA (US); Vincent Tabard-Cossa, Mountain View, CA (US); Robert W. Dutton, Palo Alto, CA (US)

(73) Assignees: The Board of Trustees of the Leland Stanford Junior University, Stanford, CA (US); The University of Ottawa, Ontario (CA)

( * ) Notice: Subject to any disclaimer, the term of this patent is extended or adjusted under 35 U.S.C. 154(b) by 200 days.

(21) Appl. No.: 14/043,710

(22) Filed: Oct. 1, 2013

(65) Prior Publication Data
US 2014/0090981 A1   Apr. 3, 2014

Related U.S. Application Data

(60) Provisional application No. 61/708,510, filed on Oct. 1, 2012.

(51) Int. Cl.
*G01N 27/447* (2006.01)
*G01N 33/48* (2006.01)
(Continued)

(52) U.S. Cl.
CPC .......... *C02F 1/4698* (2013.01); *B01D 63/088* (2013.01); *B01D 71/02* (2013.01);
(Continued)

(58) Field of Classification Search
CPC .......... G01N 27/4145; G01N 27/4146; G01N 27/447; B01D 63/088; B01L 2200/0647;
(Continued)

(56) References Cited

U.S. PATENT DOCUMENTS

| 5,082,564 A | 1/1992 | Halff et al. |
| 6,413,792 B1 | 7/2002 | Sauer et al. |

(Continued)

OTHER PUBLICATIONS

Nam, S. W.; Rooks, M. J.; Kim, K. B.; Rossnagel, S. M. Ionic Field Effect Transistors with Sub-10 nm Multiple Nanopores. Nano Lett. 2009, 9, 2044-2048 Abstract Only.

(Continued)

*Primary Examiner* — Salil Jain
(74) *Attorney, Agent, or Firm* — Foley & Lardner LLP; Cliff Z. Liu

(57) ABSTRACT

Aspects of the present disclosure are directed to the flow of analytes, particles or other materials. As consistent with one or more embodiments described herein, an apparatus includes a membrane having one or more pores in a membrane. First and second electrodes facilitate electrophoretic flow of analytes through the pore, and a third electrode controls movement of the particles in the pore by modulating the shape of an electric double layer adjacent sidewalls of pore. This modulation controls the strength of an electroosmotic field that opposes the electrophoretic flow of the analytes via the pore.

12 Claims, 24 Drawing Sheets

(51) Int. Cl.
| | |
|---|---|
| B01D 63/08 | (2006.01) |
| C02F 1/469 | (2006.01) |
| B01L 3/00 | (2006.01) |
| B01D 71/02 | (2006.01) |
| G01N 33/487 | (2006.01) |

(52) U.S. Cl.
CPC ............ *B01L 3/502761* (2013.01); *B01L 3/56* (2013.01); *B01L 3/502738* (2013.01); *B01L 3/502753* (2013.01); *B01L 2200/0647* (2013.01); *B01L 2300/0864* (2013.01); *B01L 2400/0418* (2013.01); *B01L 2400/0421* (2013.01); *B01L 2400/0487* (2013.01); *B01L 2400/0627* (2013.01); *G01N 27/447* (2013.01); *G01N 33/48721* (2013.01)

(58) Field of Classification Search
CPC ...... B01L 2400/0418; B01L 2400/0421; C02F 1/4698; C12Q 2565/629; C12Q 2565/631
See application file for complete search history.

(56) References Cited

U.S. PATENT DOCUMENTS

| | | | |
|---|---|---|---|
| 6,508,273 B1* | 1/2003 | Van Den Berg | G01N 27/44752 137/807 |
| 7,001,792 B2 | 2/2006 | Sauer et al. | |
| 2003/0116552 A1* | 6/2003 | Santoruvo | B01J 19/0093 219/209 |
| 2003/0211502 A1 | 11/2003 | Sauer et al. | |
| 2004/0074784 A1* | 4/2004 | Anex | F04B 17/00 205/674 |
| 2004/0237657 A1* | 12/2004 | Xie | G01N 27/226 73/718 |
| 2005/0252857 A1 | 11/2005 | Wilson et al. | |
| 2006/0016699 A1* | 1/2006 | Kamahori | G01N 27/4145 205/777.5 |
| 2006/0049105 A1 | 3/2006 | Max | |
| 2006/0154399 A1 | 7/2006 | Sauer et al. | |
| 2007/0178507 A1* | 8/2007 | Wu | C12Q 1/6825 435/6.12 |
| 2008/0119366 A1 | 5/2008 | Sauer et al. | |
| 2009/0283751 A1* | 11/2009 | Yang | B82Y 10/00 257/24 |
| 2009/0314718 A1 | 12/2009 | Sparrow et al. | |
| 2010/0327255 A1* | 12/2010 | Peng | B82Y 10/00 257/9 |
| 2011/0147314 A1 | 6/2011 | Kippeny et al. | |
| 2012/0031763 A1 | 2/2012 | Ohmi et al. | |
| 2012/0234679 A1* | 9/2012 | Garaj | B82Y 30/00 204/520 |
| 2012/0292496 A1* | 11/2012 | Escobedo | G01N 21/554 250/282 |
| 2012/0322076 A1* | 12/2012 | Chang | C12Q 1/6816 435/6.12 |
| 2013/0034489 A1 | 2/2013 | Gilliam et al. | |

OTHER PUBLICATIONS

Vermesh, U.; Choi, J. W.; Vermesh, O.; Fan, R.; Nagarah, J.; Heath, J. R. Fast Nonlinear Ion Transport via Field-Induced Hydrodynamic Slip in Sub-20-nm Hydrophilic Nanofluidic Transistors. Nano Lett. 2009, 9, 1315-1319.
H.-C. Chang and G. Yossifon, "Understanding electrokinetics at the nanoscale: A perspecrive", Biomicrofluidics, 012001 (2009).
E. C. Yusko, R. An, and M. Mayer, "Electroosmotic Flow Can Generate Ion Current Rectification in Nano- and Micropores". ACS Nano, p. 477 (2010).
Liu, Y.; Huber, D. E.; Dutton, R. W. Limiting and Overlimiting Conductance in Field-Effect Gated Nanopores. Appl. Phys. Lett. 2010, 96, 253108.

S.J. Kim, S.H. Ko, K. H. Kang and J. Han, "Direct seawater desalination by ion concentration polarization," Nature Nanotechnology, vol. 5, pp. 297-301 (Apr. 2010).
Garaj, S.; Hubbard, W.; Reina, A.; Kong, J.; Branton, D.; Golovchenko, J. A. Graphene as a Subnanometre Trans-Electrode Membrane. Nature 2010, 467, 190-194.
Liu, Y.; Huber, D. E.; Tabard-Cossa, V.; Dutton, R. W. Descreening of Field Effect in Electrically Gated Nanopores. Appl. Phys. Lett. 2010, 97, 143109.
Firnkes, M.; Pedone, D.; Knezevic, J.; Doblinger, M.; Rant, U Electrically Facilitated Translocations of Proteins through Silicon Nitride Nanopores: Conjoint and Competitive Action of Diffusion, Electrophoresis, and Electroosmosis. Nano Lett. 2010, 10, 2162-2167.
Stein, D.; Deurvorst, Z.; van der Heyden, F. H. J.; Koopmans, W. J. A.; Gabel, A.; Dekker, C. Electrokinetic Concentration of DNA Polymers in Nanofluidic Channels. Nano Lett. 2010, 10, 765-772.
Wanunu, M.; Morrison, W.; Rabin, Y.; Grosberg, A. Y.; Meller, A. Electrostatic Focusing of Unlabelled DNA into Nanoscale Pores Using a Salt Gradient. Nat. Nanotechnol. 2010, 5, 160-165.
Luan, B. Q.; Peng, H. B.; Polonsky, S.; Rossnagel, S.; Stolovitzky, G.; Martyna, G. Base-by-Base Ratcheting of Single Stranded DNA through a Solid-State Nanopore. Phys. Rev. Lett. 2010, 104, 238103.
Muthukumar, M. Theory of Capture Rate in Polymer Translocation. J. Chem. Phys. 2010, 132, 195101.
Kowalczyk, S. W.; Grosberg, A. Y.; Rabin, Y.; Dekker, C. Modeling the Conductance and DNA Blockade of Solid-State Nanopores. Nanotechnology 2011, 22, 315101.
Albrecht, T. How to Understand and Interpret Current Flow in Nanopore/Electrode Devices. ACS Nano 2011, 5, 6714-6725. Abstract Only.
Sadki, E. S.; Garaj, S.; Vlassarev, D.; Golovchenko, J. A.; Branton, D. Embedding a Carbon Nanotube across the Diameter of a Solid State Nanopore. J. Vac. Sci. Technol., B 2011, 29, 053001.
Venkatesan, B. M.; Bashir, R. Nanopore Sensors for Nucleic Acid Analysis. Nat. Nanotechnol. 2011, 6, 615-624.
Yusko, E. C.; Johnson, J. M.; Majd, S.; Prangkio, P.; Rollings, R. C.; Li, J. L.; Yang, J.; Mayer, M. Controlling Protein Translocation through Nanopores with Bio-Inspired Fluid Walls. Nat. Nanotechnol. 2011, 6, 253-260.
Kowalczyk, S. W.; Kapinos, L.; Blosser, T. R.; Magalhaes, T.; van Nies, P.; Lim, R. Y. H.; Dekker, C. Single-Molecule Transport across an Individual Biomimetic Nuclear Pore Complex. Nat. Nanotechnol. 2011, 6, 433-438. Abstract Only.
Powell, M. R.; Cleary, L.; Davenport, M.; Shea, K. J.; Siwy, Z. S. Electric-Field-Induced Wetting and Dewetting in Single Hydrophobic Nanopores. Nat. Nanotechnol. 2011, 6, 798-802. Abstract Only.
Jin, X. Z.; Aluru, N. R. Gated Transport in Nanofluidic Devices. Microfluid. Nanofluid. 2011, 11, 297-306.
He, Y. H.; Tsutsui, M.; Fan, C.; Taniguchi, M.; Kawai, T. Gate Manipulation of DNA Capture into Nanopores. ACS Nano 2011, 5, 8391-8397. Abstract Only.
Xie, P.; Xiong, Q.; Fang, Y.; Qing, Q.; Lieber, C. M. Local Electrical Potential Detection of DNA by Nanowire-Nanopore Sensors. Nat. Nanotechnol. 2011, 7, 119-125.
Ivanov, A. P.; Instuli, E.; McGilvery, C. M.; Baldwin, G.; McComb, D. W.; Albrecht, T.; Edel, J. B. DNA Tunneling Detector Embedded in a Nanopore. Nano Lett. 2011, 11, 279-285.
Harrer, S.; Waggoner, P. S.; Luan, B. Q.; Afzali-Ardakani, A.; Goldfarb, D. L.; Peng, H. B.; Martyna, G.; Rossnagel, S. M.; Stolovitzky, G. A. Electrochemical Protection of Thin Film Electrodes in Solid State Nanopores. Nanotechnology 2011, 22, 275304.
Venkatesan, B. M.; Estrada, D.; Banerjee, S.; Jin, X. Z.; Dorgan, V. E.; Bae, M. H.; Aluru, N. R.; Pop, E.; Bashir, R. Stacked Graphene-Al2O3 Nanopore Sensors for Sensitive Detection of DNA and DNA_Protein Complexes. ACS Nano 2012, 6, 441-450.
L. Onsager and S. Kim, "Wien Effect in Simple Strong Electrolytes", J. Phys. Chem., 61 (2) pp. 198-215 (1957). First Page Only.
P. Bergveld, "A critical evaluation of direct electrical protein detection methods," Biosensors and Bioelectronics; 6 (1):55-72 (1991).

(56) References Cited

OTHER PUBLICATIONS

F. Danneville, H. Happy, G. Dambrine, J.-M. Belquin, A. Cappy, "Microscopic noise modeling and macroscopic noise models: how good a conection?", IEEE Trans. on Electron Devices, vol. 41, No. 5, pp. 779-786 (May 1994) Abstract Only.
Soderman, O.; Jonsson, B. Electro-Osmosis: Velocity Profiles in Different Geometries with Both Temporal and Spatial Resolution. J. Chem. Phys. 1996, 105, 10300-10311. Abstract Only.
J. J. Kasianowicz, E. Brandin, D. Branton, and D. W. Deamer, "Characterization of individual polynucleotide molecules using a membrane channel," Proc. Natl. Acad. Sci., vol. 93, No. 24, pp. 13770-13773 (1996).
E. Souteyrand, J.P. Cloarec, J.R. Martin, C. Wilson, I. Lawrence, S. Mikkelsen, M.F. Laurence, "Direct detection of the hybridization of synthetic homo-oligomer DNA sequences by field effect," J. Phys. Chem. B, vol. 101, pp. 2980-2985 (1997). Abstract Only.
B. Schasfoort, S. Schlautmann, J. Hendrikse, and A. van den Berg, "Field-Effect Flow Control for Microfabricated Fluidic Networks", Science, pp. 942-945 (1999). Abstract Only.
Jung-Suk Goo, Chang-Hoon Choi, F. Danneville, E. Morifuji, H.S. Momose, Yu Zhiping, H. Iwai, T.H. Lee, and R.W. Dutton, "An accurate and efficient high frequency noise simulation technique for deep submicron MOSFETs", IEEE Trans. on Electron Devices, vol. 47, No. 12, Dec. 2000, pp. 2410-2419 (2000).
S. Howorka, S. Cheley, and H. Bayley, "Sequence-specific detection of individual DNA strands using engineered nanopores," Nature Biotechnology, vol. 19, No. 7, pp. 636-639 (2001). Abstract Only.
J. Li, D. Stein, C. McMullan, D. Branton, M. Aziz, and J. Golovshenko, "Ion-beam sculpting at nanometer length scales," Nature, 2001; 412(6843):166-169 (2001).
Meller, L. Nivon, and D. Branton, "Voltage-driven DNA translocations through a nanopore," Physical Review Letters, vol. 86, No. 15, pp. 3435-3438 (2001).
G. De Geronimo, P. O'Connor, V. Radeka, B. Yu, "Front-end electronics for imaging detectors", Nuclear Instruments and Methods in Physics Research A 471 192-199 (2001).
Chun, K. Y.; Stroeve, P. Protein Transport in Nanoporous Membranes Modified with Self-Assembled Monolayers of Functionalized Thiols. Langmuir 2002, 18, 4653-4658. Abstract Only.
M. Shim, N. Wong Shi Kam, R. Chen, Y. Li, and H. Dai, "Functionalization of Carbon Nanotubes for Biocompatibility and Biomolecular Recognition," American Chemical Society, Nano Letters, Jan. 21, 2002.
M. J. Schoning and A. Poghossian, "Recent advances in biologically sensitive field-effect transistors (BioFETs)," Analyst, vol. 127, pp. 1137-1151 (2002).
W. Huang, S. Taylor, K. Fu, Y. Lin, D. Zhang, T. Hanks, A. Rao, and Y. Sun, "Attaching Proteins to Carbon Nanotubes via Diimide-Activated Amidation," American Chemical Society, Nano Letters, Mar. 16, 2002, 2 (4), pp. 311-314 Abstract Only.
P. Bergveld, "Thirty years of ISFETOLOGY: what happened in the past 30 years and what may happen in the next 30 years," Sensors and Actuators B, vol. 88, pp. 1-20 (2003). Abstract Only.
Nakane, J. J.; Akeson, M.; Marziali, A. Nanopore Sensors for Nucleic Acid Analysis. J. Phys.: Condens. Matter 2003, 15, R1365-R1393. Abstract Only.
Dai, J. H.; Ito, T.; Sun, L.; Crooks, R. M. Electrokinetic Trapping and Concentration Enrichment of DNA in a Microfluidic Channel. J. Am. Chem. Soc. 2003, 125, 13026-13027.
A.J. Storm, J. Chen, X. Ling, and D.C. Zandbergen, "Fabrication of solid-state nanopores with single-nanometer precision," Nature Mater.; 2(8):537-540 (2003).
J. Hahm and C. M. Lieber, "Direct ultrasensitive electrical detection of DNA and DNA sequence variations using nanowire nanosensors," Nano Letters, vol. 4, No. 1, pp. 51-54 (2004).
Z. Li et al., "Sequence specific label-free DNA sensors based on silicon nanowires," Nano Letters, vol. 4, pp. 245-247 (2004).
Laser and Santiago, "A Review of Micropumps," J. Micromech. Microeng. 14 (2004) R35-R64.
Nawrocki, J.; Dunlap, C.; McCormick, A.; Carr, P. W.; Part, I. Chromatography Using Ultra-stable Metal Oxide-Based Stationary Phases for Hplc. J. Chromatogr., A 2004, 1028, 1-30. Abstract Only.
Karnik, R.; Fan, R.; Yue, M.; Li, D. Y.; Yang, P. D.; Majumdar, A. Electrostatic Control of Ions and Molecules in Nanofluidic Transistors. Nano Lett. 2005, 5, 943-948.
H. Daiguji, Y. Oka, and K. Shirono, "Nanofluidic Diode and Bipolar Transistor". Nano Letters, 2274 (2005). Abstract Only.
Meagher, R. J.; Won, J. I.; McCormick, L. C.; Nedelcu, S.; Bertrand, M. M.; Bertram, J. L.; Drouin, G.; Barron, A. E.; Slater, G. W. End-Labeled Free-Solution Electrophoresis of DNA. Electrophoresis 2005, 26, 331-350.
Chun, K. Y.;Mafe, S.; Ramirez, P.; Stroeve, P. Protein Transport through Gold-Coated, Charged Nanopores: Effects of Applied Voltage. Chem. Phys. Lett. 2006, 418, 561-564. Abstract Only.
Karnik, R.; Castelino, K.; Majumdar, A. Field-Effect Control of Protein Transport in a Nanofluidic Transistor Circuit. Appl. Phys. Lett. 2006, 88, 123114. Abstract Only.
M. C. Cheng et al., "Nanotechnologies for biomolecular detection and medical diagnostics," Current Opinion in Chemical Biology, vol. 10, pp. 11-19 (2006).
A. Talasaz, M. Nemat-Gorgani, Y. Liu, P. Stahl, R.W. Dutton, M. Ronaghi, and R.W. Davis, "Prediction of protein orientation upon immobilization on biological and nonbiological surfaces," Proc Natl Acad Sci, 103(40):14773-8 (2006).
E. Stern et al., "Label-free immunodetection with CMOS-compatible semiconducting nanowires," Nature, vol. 445, pp. 519-522 (2007).
Gracheva, M. E.; Vidal, J.; Leburton, J. P. p_n Semiconductor Membrane for Electrically Tunable Ion Current Rectification and Filtering. Nano Lett. 2007, 7, 1717-1722.
He, J.; Lin, L.; Zhang, P.; Lindsay, S. Identification of DNA Basepairing via Tunnel-Current Decay. Nano Lett. 2007, 7, 3854-3858.
A. Holtzel and U. Tallarek, "Ionic conductance of nanopores in microscale analysis systems: where microfluidics meets nanofluidics.", J. Sep. Sci., 1398 (2007). Abstract Only.
S. Kim, Y.-C. Wang, J. Lee, H. Jang, and J. Han, "Concentration Polarization and Nonlinear Electrokinetic Flow near Nanofluidic Channel", Phys. Rev. Lett., 044501 (2007).
Dekker, C. "Solid-State Nanopores." Nat. Nanotechnol. 2007, 2, 209-215, Abstract Only.
Branton, D.; Deamer, D. W.; Marziali, A.; Bayley, H.; Benner, S. A.; Butler, T.; Di Ventra, M.; Garaj, S.; Hibbs, A.; Huang, X. H.; et al. The Potential and Challenges of Nanopore Sequencing. Nat. Biotechnol. 2008, 26, 1146-1153.
Y. Liu, J. Sauer, and R. Dutton, "Effect of Electrodiffusion Current Flow on Electrostatic Screening in Aqueous Pores," J. Appl. Phys. 103, pp. 084701-1-084701-03 (2008).
Y. Liu, K. Lilja, C. Heitzinger, and R. Dutton, "Overcoming the Screening-Induced Performance Limits of Nanowire Biosensors: A Simulation Study on the Effect of Electro-Diffusion Flow," Electron Devices Meeting, IEDM 2008, IEEE International, pp. 1-4 (2008).
P. R. Nair and M. A. Alam, "Screening-limited response of nanobiosensors," Nano Letters, vol. 8, No. 5, pp. 1281-1285 (2008).
C. Bouzigues, P. Tabeling, and L. Bocquet, "Nanofluids in the Debye Layer at Hydrophilic and Hydrophobic Surfaces", Phys. Rev. Lett., 101, 114503 (2008).
M. Gracheva, D. Melnikov, and J. Leburton, "Multilayered Semiconductor Membranes for Nanopore Ionic Conductance", ACS Nano, 2349 (2008).
E. Kalman, I. Vlassiouk, and Z. Siwy, "Nanofluidic Bipolar Transistors", Advanced Materials, 293 (2008). Abstract Only.
R. Fan, S. Huh, R. Yan, J. Arnold, and P. Yang, "Gated proton transport in aligned mesoporous silica films" Nature Mater., 303 (2008).
Zhou, K. M.; Kovarik, M. L.; Jacobson, S. C. Surface-Charge Induced Ion Depletion and Sample Stacking near Single Nanopores in Microfluidic Devices. J. Am. Chem. Soc. 2008, 130, 8614-8616. Abstract Only.
Sparreboom, W.; van den Berg, A.; Eijkel, J. C. T. Principles and Applications of Nanofluidic Transport. Nat. Nanotechnol. 2009, 4, 713-720. Abstract Only.

(56) References Cited

OTHER PUBLICATIONS

E. Kalman, O. Sudre, I. Vlassiouk, and Z. Siwy, "Control of ionic transport through gated single conical nanopores", Anal. Bioanal. Chem., 413 (2009).

M. Taniguchi, M. Tsutsui, K. Yokota, and T. Kawai, "Fabrication of the gating nanopore device". Appl. Phys. Lett., , 123701 (2009). Abstract Only.

Tabard-Cossa, V.; Wiggin, M.; Trivedi, D.; Jetha, N. N.; Dwyer, J. R.; Marziali, A. Single-Molecule Bonds Characterized by Solid-State Nanopore Force Spectroscopy. ACS Nano 2009, 3, 3009-3014.

\* cited by examiner

FLOW CONTROL METHOD AND APPARATUSES

BACKGROUND

Nanopore devices that manipulate ionic and biomolecular transport, such as surface modification of a nanopore wall, can impact biomolecular translocation. Electrowetting has been used to reversibly open and close hydrophobic nanopores and gated nanopores have modulated ionic current and offered the prospect of greater control over molecular translocation. Additionally, control of biomolecular capture and transport has been limited.

Observed modulations have relied on extreme biasing conditions (~VG~100 V) that are impractical for biosensing applications and detrimental to the device integrity. Further, the underlying mechanism is not well explored.

SUMMARY

Various aspects of the present disclosure are directed toward controlling flow of analytes, such as chemicals, biological materials or other particles. Certain embodiments are directed toward controlling flow using electroosmotic flow (EOF) to counter electrophoresis. For instance, in certain embodiments, a membrane has at least one pore defined by sidewalls extending between opposing surfaces of the membrane. A pair of electrodes facilitates electrophoretic flow of analytes through the pore, and a third electrode controls the movement of the analytes by modulating the shape of an electric double layer adjacent the sidewalls and within the pore. This modulation controls the strength of an electroosmotic flow that opposes the electrophoresis.

A more particular example embodiment is directed to an apparatus including a membrane having one or more pores defined by sidewalls extending between opposing surfaces of the membrane, first and second electrodes that facilitate electrophoretic flow of analytes through the pore, and a third electrode that controls the movement of the analytes. More specifically, the third electrode modulates the shape of an electric double layer adjacent sidewalls of the pore, and thereby controls the strength of an electroosmotic field that opposes movement of the analytes via the pore.

Another example embodiment is directed to an apparatus including a membrane having at least one fluidic pore defined by sidewalls extending between opposing surfaces of the membrane, source and drain electrodes that facilitate electrophoresis of biomolecules through the fluidic pore, and a gate electrode that controls movement of the biomolecules. Specifically, the gate electrodes modulates the shape of an electric double layer adjacent the sidewalls and within the fluidic pore, thereby controlling the strength of an electroosmotic fluid flow that opposes electrophoresis of the biomolecules via the fluidic pore.

Another example embodiment is directed to a method in which first and second electrodes are used to facilitate movement of analytes through a pore in a membrane, in which the pore is defined by sidewalls extending between opposing surfaces of the membrane. A bias is applied at the pore to control movement of the analytes, in which the bias modulates the shape of an electric double layer adjacent the sidewalls and within the pore. This modulation controls the strength of an electroosmotic fluid flow that opposes said movement of the analytes via the pore.

Additionally, various aspects of the present disclosure are also directed toward using electrically gated pores as a reversible electronically-tunable biomolecular switch. This provides effective electrokinetic control of material (e.g., nucleic acid) capture with >1000-fold modulation using sub-1 V gate biases. Certain aspects of the present disclosure are utilized to exploit barrier-limited operation arising from the balanced interplay between electroosmotic flow (EOF) and electrophoresis. Additionally, certain embodiments of the present disclosure vary a gate voltage to modulate the shape of an electric double layer (EDL) to finely tune the strength of the EOF opposing the electrophoretic motion of the object that is to be captured (e.g., DNA). Operating these so-called nanofluidic transistors (NFTs) within the sub- to near-threshold regime allows for exponential (or superlinear) control of an objects capture rate.

BRIEF DESCRIPTION OF THE DRAWINGS

The disclosure may be more completely understood in consideration of the detailed description of various embodiments of the disclosure that follows in connection with the drawings, each being consistent with one or more of these embodiments, in which.

Figure 1A:
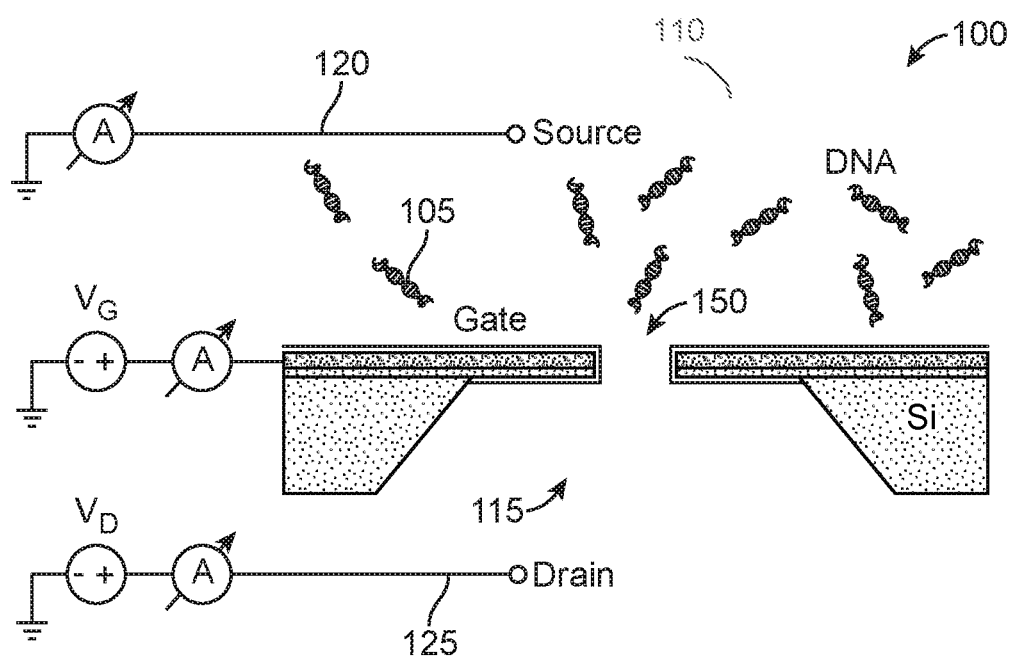
FIG. 1A shows an example nanofluidic transistor (NFT) apparatus, consistent with various aspects of the present disclosure.

While the disclosure is amenable to various modifications and alternative forms, specifics thereof have been shown by way of example in the drawings and are described in detail herein (including in the Appendices filed in the underlying provisional application). It should be understood that the intention is not to necessarily limit the disclosure to the particular embodiments described. On the contrary, the intention is to cover all modifications, equivalents, and alternatives falling within the spirit and scope of the disclosure.

DESCRIPTION OF EMBODIMENTS

Various aspects of the present disclosure are directed toward apparatuses, methods, and systems useful in electrostatic control of a capturing of materials such as nucleic acids, particles or other analytes.

Certain embodiments of the present disclosure are directed toward apparatuses which include a membrane having at least one pore defined by sidewalls extending between opposing surfaces of the membrane. These apparatuses also include first and second electrodes that facilitate electrophoresis of analytes (e.g., particles) through the pore(s). Further, a third electrode is also included in apparatuses of the present disclosure. The third electrode controls movement of the analytes by modulating the shape of an electric double layer (EDL) adjacent the sidewalls and within the pore. The modulation controls the strength of an electroosmotic flow that opposes the electrophoresis of the analytes via the pore. In certain more specific embodiments, the third electrode modulates the shape of the electric double layer by changing a surface potential of the sidewalls and controlling the density of ions near the surface. Additionally, in other embodiments, the third electrode modulates the shape of the electric double layer to pull analytes from the electrophoretic flow of particles via the pore, and holds the analytes near a surface of the sidewalls.

Further embodiments of the present disclosure include an additional fourth electrode. In such embodiments, the fourth electrode controls movement of the analytes by modulating the shape of an electric double layer adjacent the sidewalls and within the pore and thus controls the strength of an electroosmotic flow that opposes electrophoresis via the pore. Additionally, various embodiments of the present disclosure include a fourth electrode arranged with the third electrode to control movement of the analytes by modulating the shape of an electric double layer adjacent the sidewalls and within the pore. This action controls the strength of an electroosmotic flow that opposes electrophoresis of the analytes via the pore. Moreover, in embodiments of the present disclosure having such a third and fourth electrode arranged together, these electrodes are operated to differently modulate the shape of the electric double layer.

Apparatuses of the present disclosure, in certain embodiments, include electrodes that control the electrophoresis of analytes as discussed above by modulating the shape of electric double layers adjacent the sidewalls and within the pore, thereby controlling the strength of an electroosmotic flow that opposes the electrophoresis. For instance, when third and fourth electrodes are used in this regard, each electrode modulates a respective electric double layer, such that the respective electrodes and/or double layers may be different. Further, in certain embodiments, respective reservoirs provide and accept the analytes for electrophoresis thereof.

In some embodiments, such an apparatus also includes a sensor that senses a characteristic of analytes in the pore. Apparatuses of the present disclosure that contain a sensor include, in certain more specific embodiments, a signal processing circuit that processes a signal from the sensor to provide an indication of the sensed characteristic. The electroosmotic flow may be controlled, for example, to maintain particles within proximity of the sensor to facilitate sensing thereof.

Aspects of the present disclosure are also directed toward an apparatus that includes a membrane having at least one fluidic pore, such as a nanofluidic pore, defined by sidewalls extending between opposing surfaces of the membrane. Source and drain electrodes are provided with such an apparatus to facilitate electrophoresis of biomolecules through the fluidic pore. Additionally, the flow of biomolecules is controlled by a gate electrode by modulating the shape of an electric double layer adjacent the sidewalls and within the fluidic pore and thereby controlling the strength of an electroosmotic field that opposes electrophoresis of the biomolecules via the fluidic pore(s).

Various embodiments are directed to methods in accordance with the following description of various apparatuses, in which particle flow is controlled as described (e.g., with such methods using one or more apparatuses as described and/or one or more similar apparatuses).

In certain embodiments of the present disclosure, nanofluidic transistor (NFT) devices include a 4×4 array of pores in a $SiN_x$ membrane. The pores are covered on one side by a sputtered Au film coated with conformal $Al_2O_3$ (e.g., formed by atomic layer deposition (ALD)). In certain example embodiments, an NFT device is provided with a 140 nm thick membrane and approximately 200 nm pores. In other example embodiments, an NFT device is provided with 80 nm thick membranes and approximately 160 nm pores. In certain embodiments, the aspect ratios allow for NFT devices of the present disclosure to operate in a barrier-limited regime, in addition to relaxing their fabrication constraints. Other embodiments of the present disclosure include NFT devices manufactured with varying membrane thicknesses and pore sizes that maintain such an aspect ratio.

FIG. 1 shows an example schematic drawing of an NFT 100 where DNA molecules 105 flow from the source reservoir 110 into the drain reservoir 115. More specifically, FIG. 1A shows an example NFT in buffered 10 mM NaCl solution. The source well 120 is grounded through an Au or an Ag/AgCl electrode and contains 2.5 nM of 100 bp DNA fragments. The drain well 125 has +800 mV applied. FIG. 1B shows two example embodiments of NFTs: 140 nm thick membrane and approximately 200 nm fluidic pore (150); and 80 nm thick membranes and approximately 160 nm fluidic pores (160). The NFT (150) having 140 nm thick membrane includes a 30 nm thick $SiN_x$, and 80 nm of gate material surrounded by 15 nm of $Al_2O_3$ deposited by ALD. A pore 170 in the membrane is a larger pore which includes a region occupied by the $Al_2O_3$ deposited on a sidewall of the pore 170, and the fluidic pore 150 is a smaller pore within the pore 170 and excludes the region occupied by the $Al_2O_3$ deposited on the sidewall of the pore 170. The NFT (160) having a 80 nm thick membrane includes a 10 nm thick $SiN_x$, and 50 nm of gate material surrounded by 10 nm $Al_2O_3$. A pore 170 in the membrane is a larger pore which includes a region occupied by the $Al_2O_3$ deposited on a sidewall of the pore 170, and the fluidic pore 160 is a smaller pore within the pore 170 and excludes the region occupied by the $Al_2O_3$ deposited on the sidewall of the pore 170. FIG. 1C depicts an example schematic of nanopores 170, milled by FIB, which are 500 nm apart in a 4×4 square pattern. FIG. 1D depicts an SEM image of the array described in FIG. 1C. The scale bar is 500 nm.

In certain embodiments, a 4×4 array of pores is used as opposed to a single pore. The array of pores increases the molecular flux as application for the purpose of e.g., a quantitative polymerase chain reaction (qPCR) that can be used to quantify the amount of DNA captured and translocated.

In an example embodiment of the present disclosure, a "thick" NFT device (150) was fabricated from 50×50 μm, 30 nm thick free-standing $SiN_x$ membranes supported on a 200 μm thick silicon frame. On the $SiN_x$ side, a 75 nm thick Au film is deposited on top of a 5 nm thick Cr adhesion layer by sputtering to serve as the gate electrode. A 4×4 array of pores 170, with a diameter of approximately 200 nm, is milled by, for example, a focused ion beam. Subsequently, a 15 nm of $Al_2O_3$ is deposited by ALD to insulate the gate and prevent direct leakage currents. In such an embodiment, the total thickness of the NFT is approximately 140 nm, however, chip-to-chip process variation can result in some of the NFT being slightly thinner (e.g., as thin as 130 nm). This embodiment of an NFT device is referred to as the "140 nm" or "thick" NFT.

Additionally, in other embodiments, an NFT device is manufactured by sputtering 45 nm of Au (with an additional 5 nm Cr adhesion layer) on 10 nm $SiN_x$ membranes. Using a shadow mask, an additional 100 nm of Au is deposited on one of the corners of these chips to serve as a bond pad. A 4×4 array of pores 170, with a diameter of approximately 160 nm, is milled by FIB. 10 nm of $Al_2O_3$ is deposited by ALD to insulate the gate, for a total device thickness of 80 nm. This embodiment of an NFT device is referred to as the "80 nm" NFT or thin NFT (160).

Figure 2A:
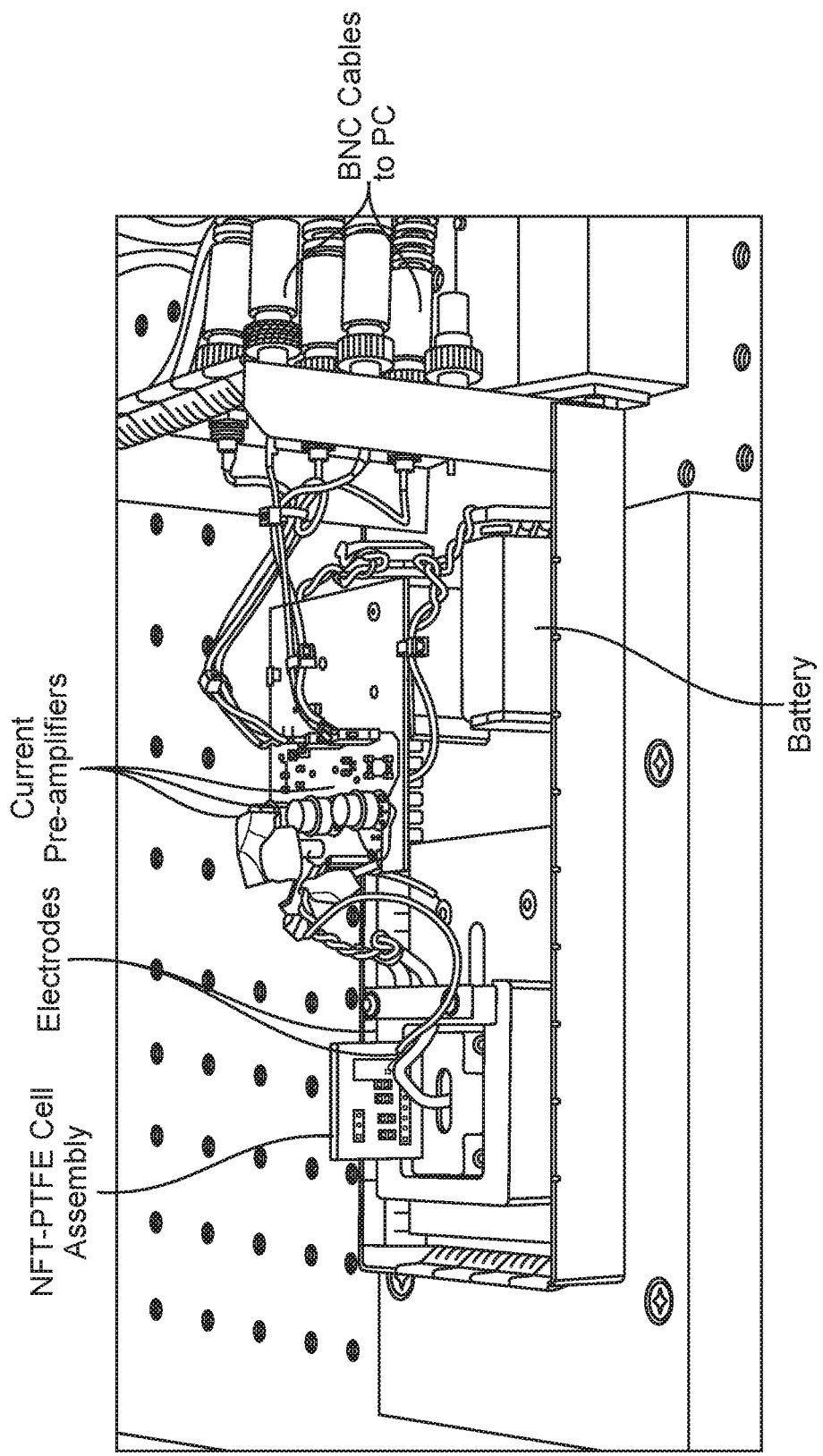
FIG. 2A shows an example NFT assembly, consistent with various aspects of the present disclosure.
Figure 2B:
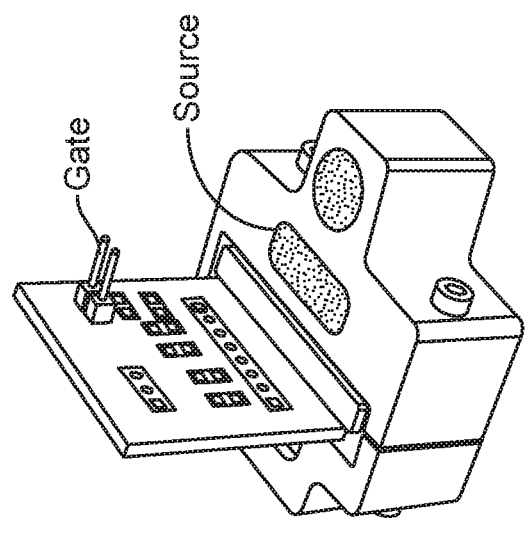
FIG. 2B shows chips implementing a NFT assembly, consistent with various aspects of the present disclosure.
Figure 2B:
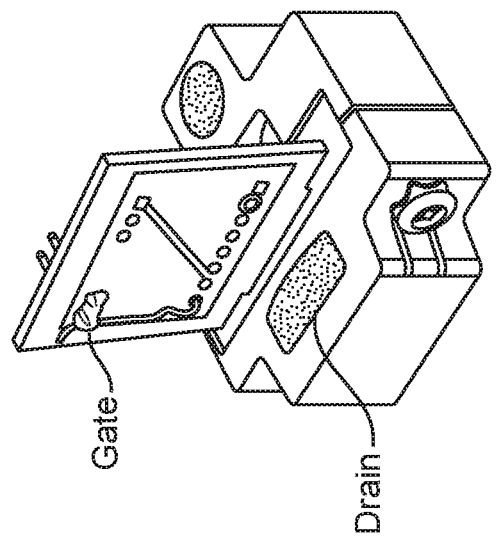

As shown in FIGS. 2A-2B, various embodiments of the present disclosure include mounting NFT devices onto printed circuit boards (PCBs) to make electrical contact to the gate electrode. The NFT device and PCB combinations are immersed into liquids in polytetrafluoroethylene (PTFE) cells that form source and drain reservoirs. In certain embodiments, a compact-battery-powered custom-built instrument is used to apply voltages and measure the current at each electrode (drain, gate, source). This embodiment includes three independent current amplifiers on a PCB housed in a copper Faraday cage.

In various experimental embodiments of the present disclosure, the drain voltage ($V_D$) is fixed (e.g., at +800 mV), and the gate voltage ($V_G$) is varied (e.g., between 0 V and +500 mV). Multiple gate voltage sweeps, from low $V_G$ to high $V_G$, are made for each NFT device embodiment, in order to confirm the reproducibility of the gate control. DNA flows from the source well into the drain well. In certain experimental embodiments, two Au or Ag/AgCl electrodes are used to apply a bias between the drain and the source, and the wells are filled with buffered 10 mM NaCl solutions. At the start of the experiments, DNA is injected into the source well, setting the concentration at 2.5 nM. Following application of electrical biases at the drain and gate electrodes, three timed samples from the drain well are taken at 10 min intervals.

Figure 3:
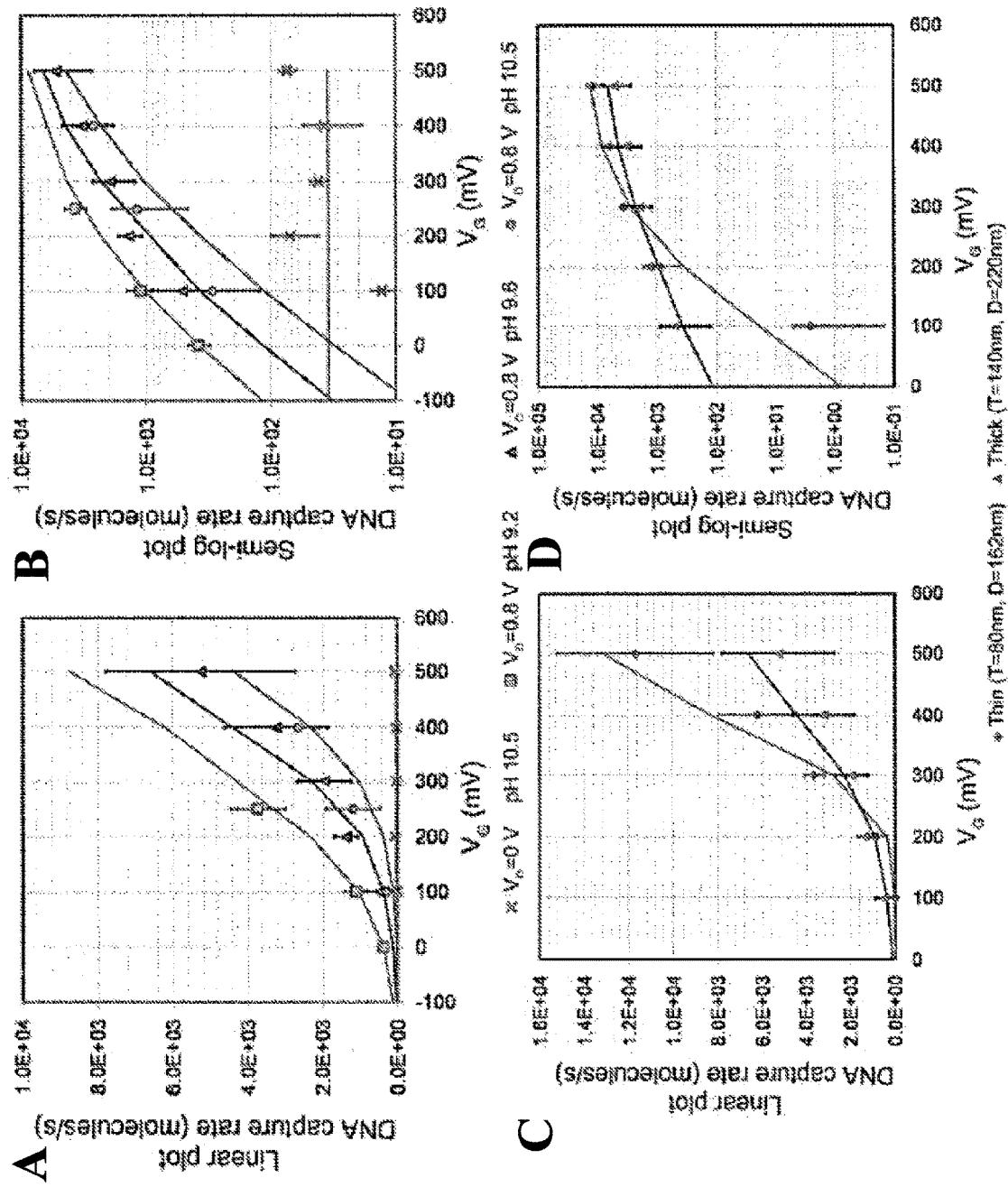
FIG. 3 shows four plots of experimental results of DNA capture rate versus voltage compared to stimulation using NFT apparatuses, consistent with various aspects of the present disclosure.

FIG. 3 shows experimental results of DNA capture rate versus $V_G$ compared to simulation. The markers represent the experimental results. The error bars are standard deviations of experimental results. Simulated results are shown as solid lines. FIG. 3A of depicts a plot of DNA capture rate versus $V_G$ for various solution pHs of a "thick" NFT devices. When $V_D$=+800 mV, $V_G$ is able to control DNA capture rate of the nanofluidic transistor (NFT) by altering the counterion concentration. Further, the solution pH also alters pore surface charge. Thus, changing pH results in shifting the DNA capture threshold. In simulations, this pH dependence is modeled by assigning different surface charge densities (See, e.g., Table 1, below). Additionally, experimentation was also performed when $V_D$=0 V, which resulted in the net translocation rate being small, approximately 50/s. FIG. 3B depicts a semilog plot of the results shown in FIG. 3A.

TABLE 1

Simulation Parameters that are changed according to the different experimental runs in FIG. 3

| Parameter | Thick, pH 9.2 | Thick, pH 9.6 | Thick, pH 10.5 | Thin, pH 9.6 |
|---|---|---|---|---|
| Pore Diameter | 200 nm | 200 nm | 200 nm | 150 nm |
| Gate Thickness | 80 nm | 80 nm | 80 nm | 50 nm |
| Top Insulator Thickness | 15 nm | 15 nm | 15 nm | 10 nm |
| Bottom Insulator Thickness | 45 nm | 45 nm | 45 nm | 20 nm |
| Gate Insulator Thickness | 15 nm | 15 nm | 15 nm | 7 nm |
| Surface charge density, $\sigma_s$ | $-8.50 \times 10^{-2}$ q/nm$^2$ | $-8.75 \times 10^{-2}$ q/nm$^2$ | $-9.00 \times 10^{-2}$ q/nm$^2$ | $-1.025 \times 10^{-1}$ q/nm$^2$ |
| Zeta-potential | -0.0515 V | -0.0504 V | -0.0493 V | -0.0558 V |

In FIGS. 3A and 3B, the data points are the averages of the measured capture rates for each experimental condition (with the error bars being the standard deviations). The solid lines are the capture rates determined from the device level simulations. The gate voltage on the "thick" devices reversibly modulates the DNA capture rate by approximately 10× with sub-1 V gate bias. For pH 9.2, the increase from 390/s to 3800/s is seen for a $\Delta V_G$ of 250 mV. For pH 9.6, an increase from 520/s to 5300/s is seen for a $\Delta V_G$ of 400 mV. For pH 10.5, an increase from 300/s to 2600/s is observed for a $\Delta V_G$ of 300 mV. This control is super-linear versus $V_G$, as expected from a barrier-limited operation. Given a gate bias ($V_G$), the capture rate decreases with increasing pH. Thus, by adjusting the pH, one can tune the threshold voltage on $V_G$, beyond which the NFT switches on to allow biomolecule translocation. Further, fixing $V_D$=0 V while varying $V_G$ shows that the diffusive translocation rate of DNA is small, ca. 50/s, ruling out diffusion as the primary transport mechanism. The simulation also predicts an unmodulated diffusive translocation rate of 40/s in this control case.

Figure 1B:
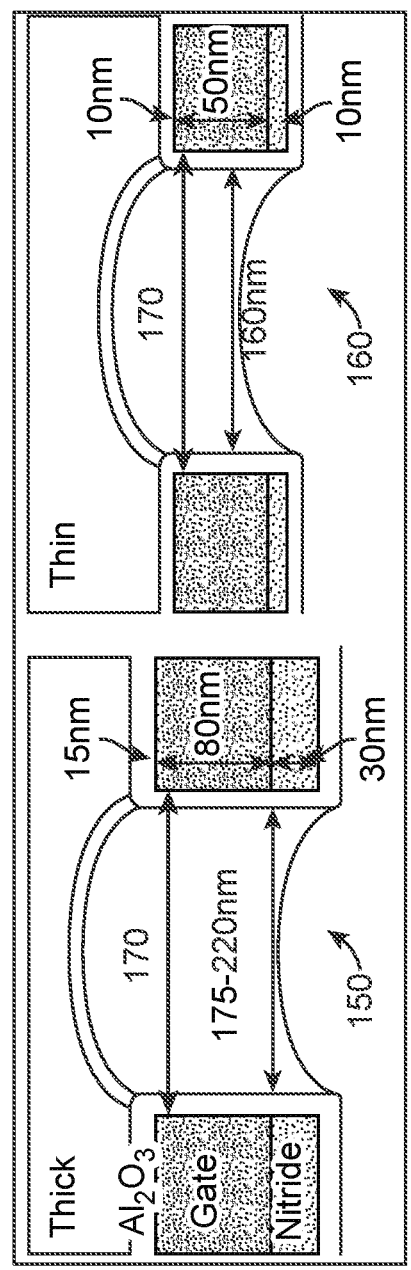
FIG. 1B shows two example NFT apparatuses, consistent with various aspects of the present disclosure.
Figure 1C:
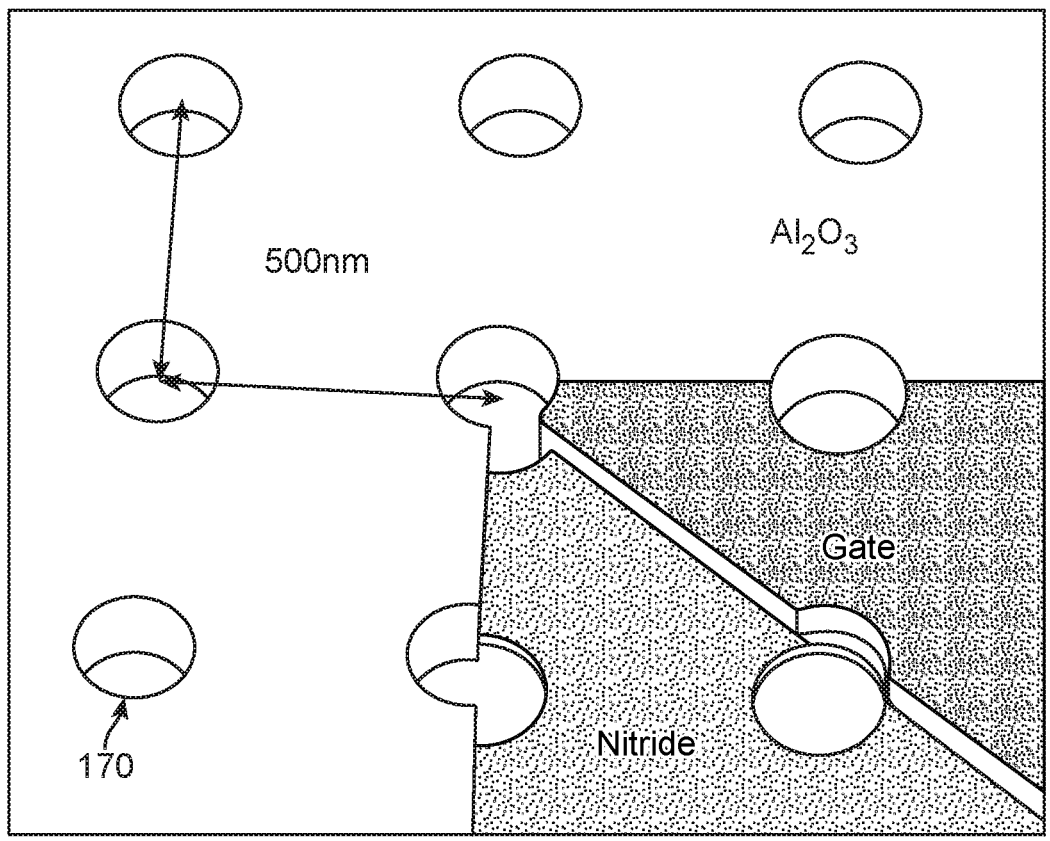
FIG. 1C shows an example configuration of pores in NFT apparatuses, consistent with various aspects of the present disclosure.
Figure 1D:
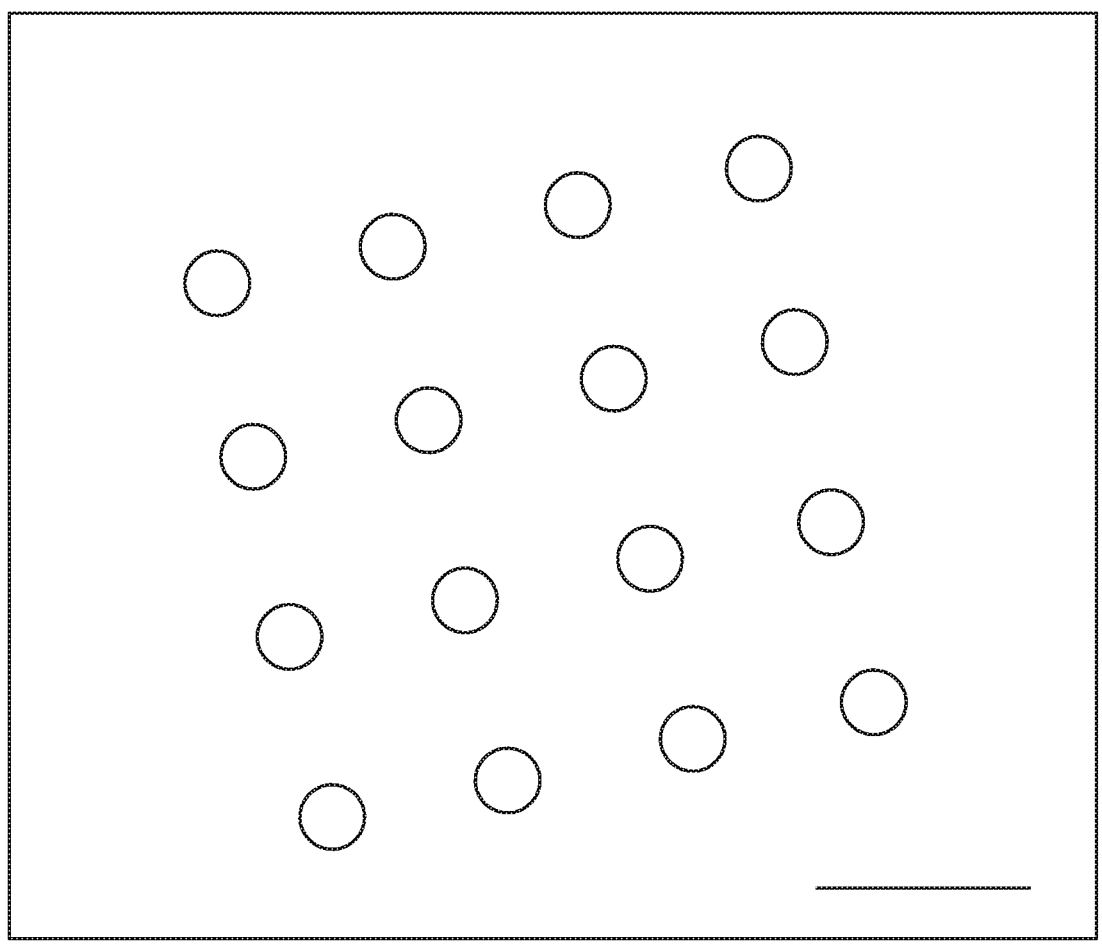
FIG. 1D shows a scanning electron micrograph (SEM) image of pores in NFT apparatuses, consistent with various aspects of the present disclosure.

In certain experimental embodiments, in an effort to further enhance biomolecular capture modulation, the gate control is increased by employing the "thin" NFT, where the membrane thickness is reduced from 140 to 80 nm, the pore diameter from 220 to 160 nm, and the gate oxide thickness from 15 to 10 nm (e.g., as shown in FIG. 1B). Due to the over potential of Au source/drain electrodes used for the thick NFTs, the measured ionic current for the thick NFT was depressed compared to measurements performed with Ag/AgCl electrodes, though this does not appear to hinder the DNA capture rate modulation. Nevertheless, for the "thin NFT," nonpolarizable Ag/AgCl electrodes were used instead to monitor the ionic current through the pores. At pH 9.6, the "thick" devices show capture rate modulation from 520/s when $V_G$=+100 mV to 5300/s when $V_G$=+500 mV, whereas the "thin" NFT devices range from 2.5/s to 12000/s under the same conditions, a 4000× modulation as shown in FIGS. 3C and 3D. More specifically, FIG. 3C shows a plot of DNA capture rate versus $V_G$ of NFTs before and after the design revision to enhance modulation. Both devices are in solution with pH 9.6. The "thin" device, with smaller diameter pores and a thinner gate dielectric film, has enhanced gate control. The application of the same $V_D$ across a thinner membrane results in larger transmembrane electric field as well. This results in stronger relative EOF that can turn the device off at low $V_G$ and have larger capture rate at high $V_G$. FIG. 3D shows a semilog plot of the results shown in FIG. 3C. Accordingly, embodiments of the present disclosure of the "thin" NFT provide improved modulation amplitude, and offer a superior shut off state for biomolecular passage at low $V_G$.

In order to analyze device operation and monitor the condition of the gate electrode, currents can be simultaneously measured at all three electrodes. After being immersed in buffered 10 mM NaCl, each 4×4 array of pores was characterized to check for linear current-voltage (I-V) characteristics, conductance stability, and noise. Currents were recorded at a 10 kHz sampling frequency, and the signals were software filtered at 1 kHz. For large pores, in low salt concentrations, the conductance was estimated to be based on geometrical factors (e.g., approximating the actual pore shapes as cylinders and taking access resistance into account) and the surface charge. For instance, the expression for the NFT pore conductance can be derived based on an equivalent analogue circuit having the output of an $R_{access}/2$ resistor connected in series with an $R_{surface\ charge}$ resistor that is in parallel with an $R_{pore\ cylinder}$, the output of which is also connected to another $R_{access}/2$ resistor. The values for each of the resistors are as follows:

$$R_{access}/2 = \frac{1}{2\sigma d}$$

$$R_{pore\ cylinder} = \frac{4l}{\pi\sigma d^2}$$

$$R_{surface\ charge} = \frac{l}{\pi\mu + pd}$$

Under these approximations the conductance, G, can be calculated with the following expression:

$$G = \frac{\pi\sigma d(\sigma d + 4\mu + \rho)}{4l\sigma + \pi(\sigma d + 4\mu + \rho)} \quad (1)$$

where d is the diameter of the pore, l is the thickness of the membrane, μ is the mobility of the counterion, p is the surface charge density, and σ is the bulk conductivity. This formula gives an estimated conductance of approximately 30 nS for a single pore, or 480 nS for the array of the thin NFT. This is in reasonable agreement with the experimental value of ~550 nS, considering the simplification of the model, not accounting for secondary geometric effects or the presence of the gate electrode which causes local redistributions of ions inside the pores. The conductance stability is verified for all of the NFT devices before and after DNA capture experiments.

Figure 4:
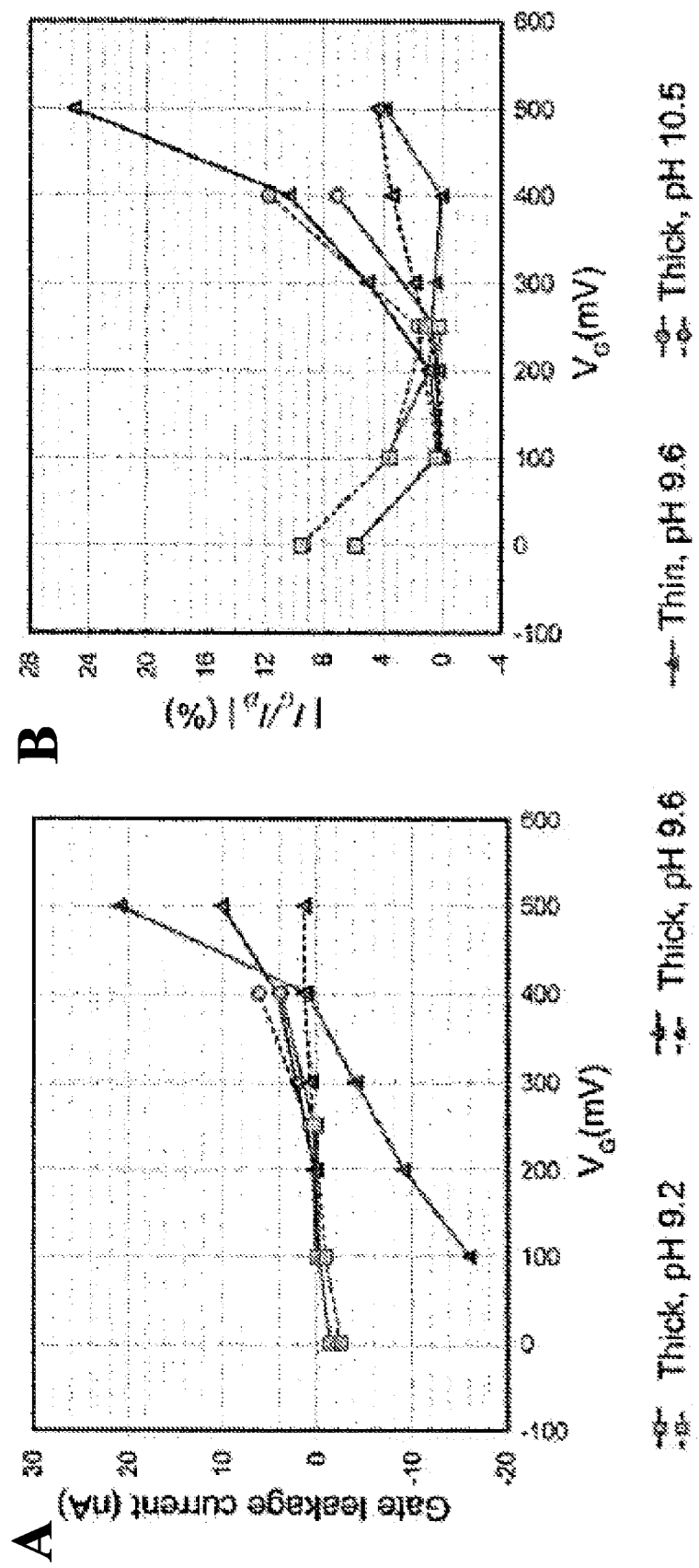
FIG. 4 shows two plots of experimental results of average currents in DNA translocation experiments, consistent with various aspects of the present disclosure.
Figure 5:
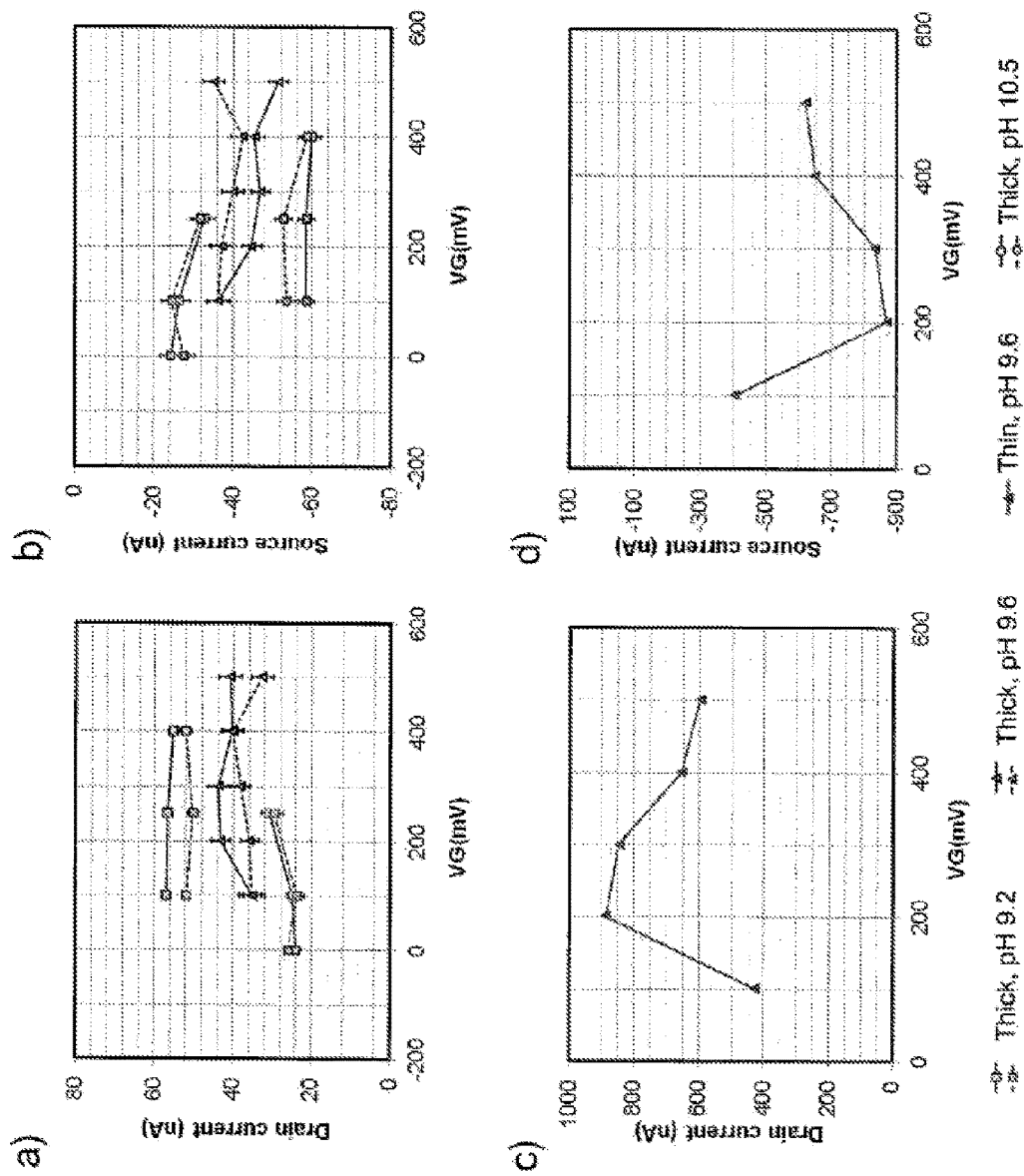
FIG. 5 shows example time-averaged drain and source ionic currents during the DNA capture rate modulation experiments, consistent with various aspects of the present disclosure.
Figure 6A:
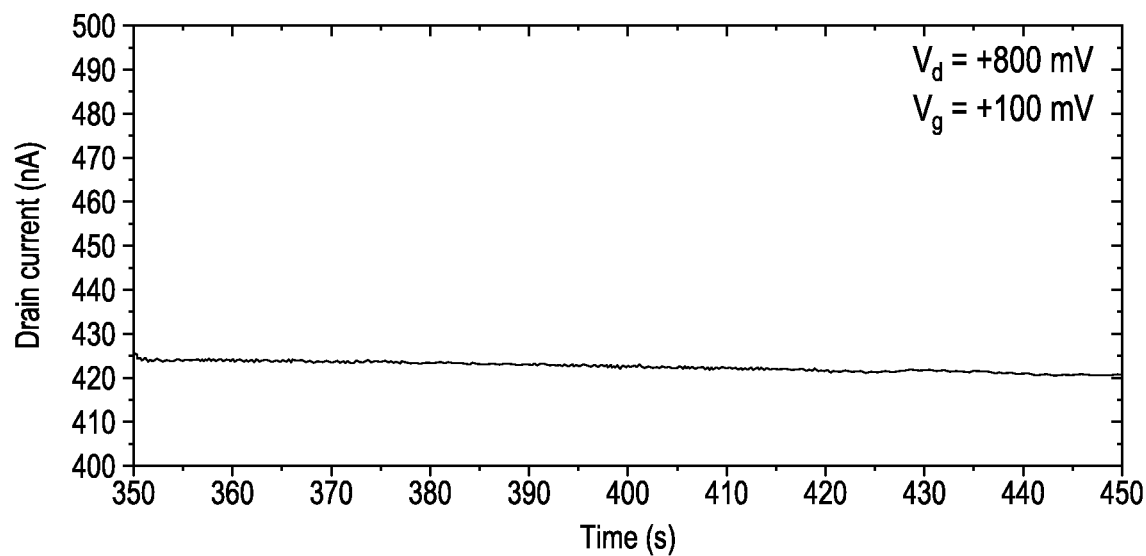
FIG. 6A-6J show example current-time traces at the drain and the gate electrodes of the thin device, consistent with various aspects of the present disclosure.
Figure 6B:
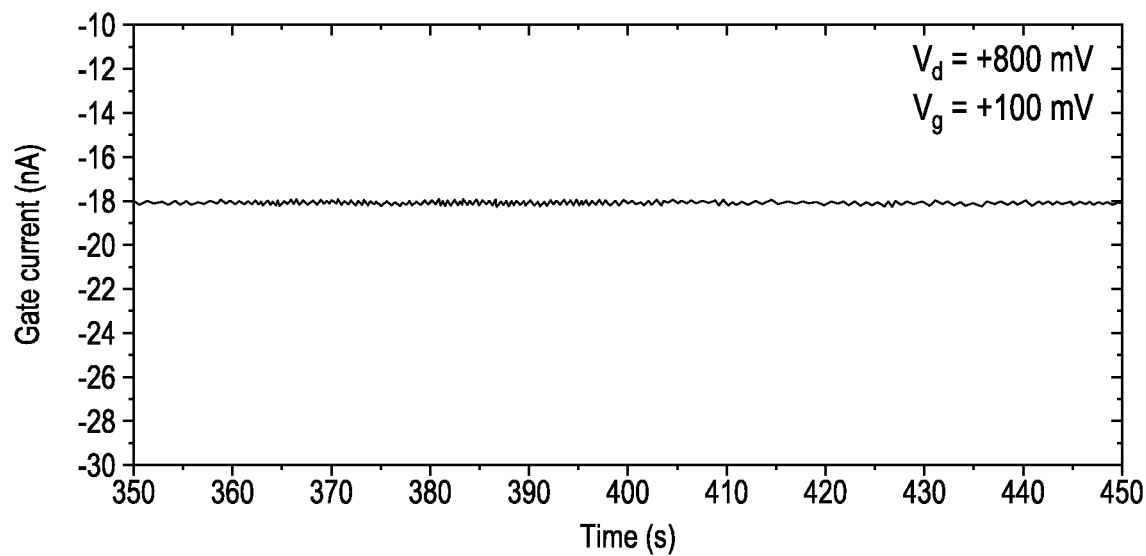
Figure 6C:
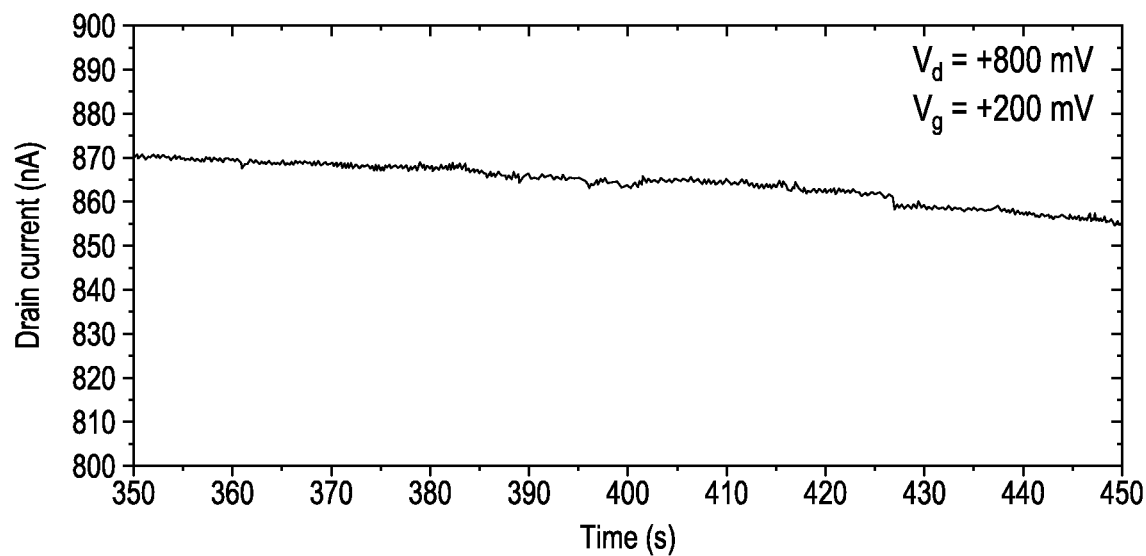
Figure 6D:
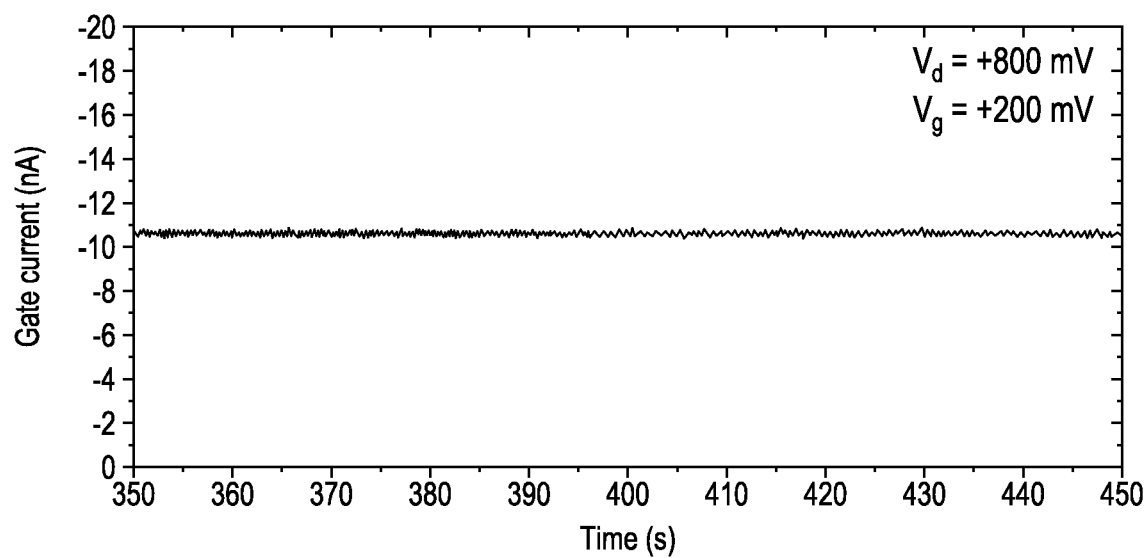
Figure 6E:
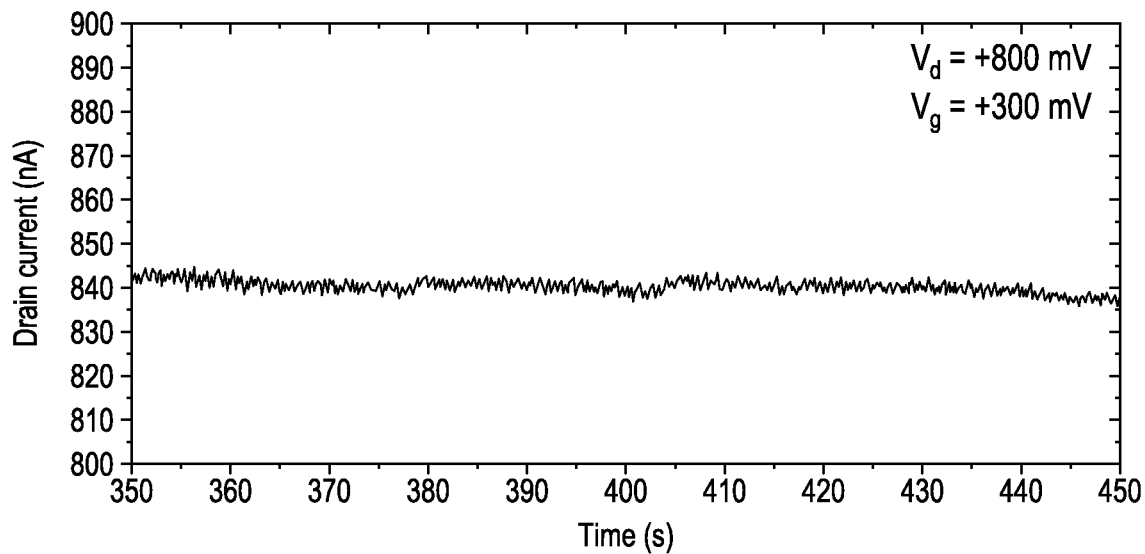
Figure 6F:
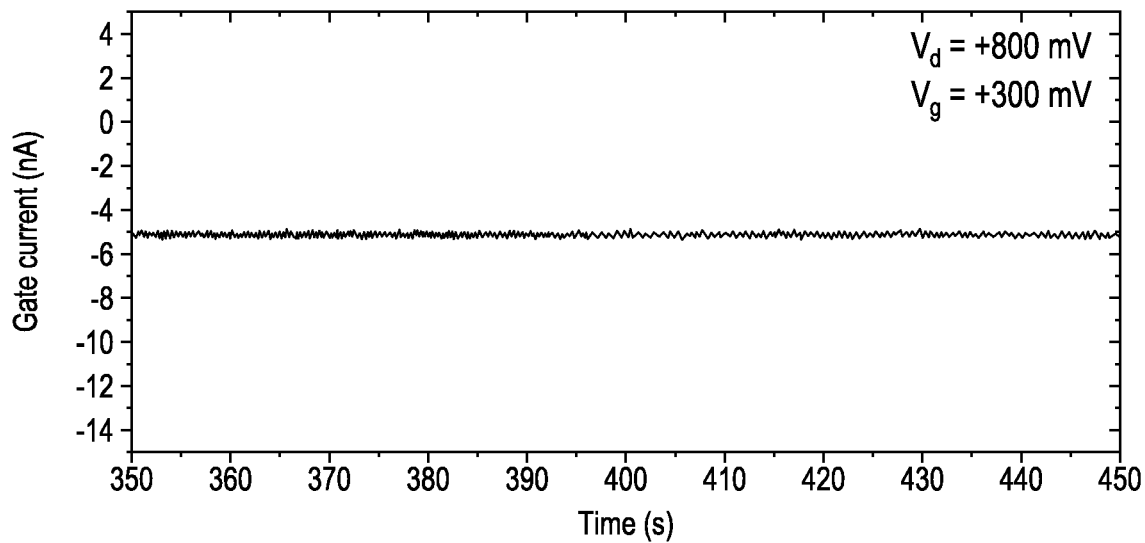
Figure 6G:
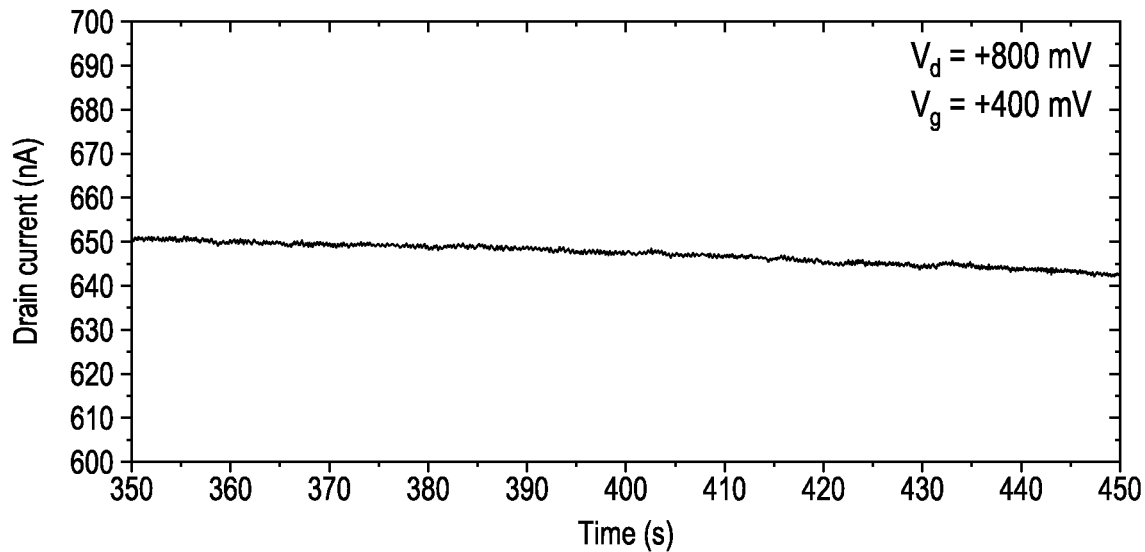
Figure 6H:
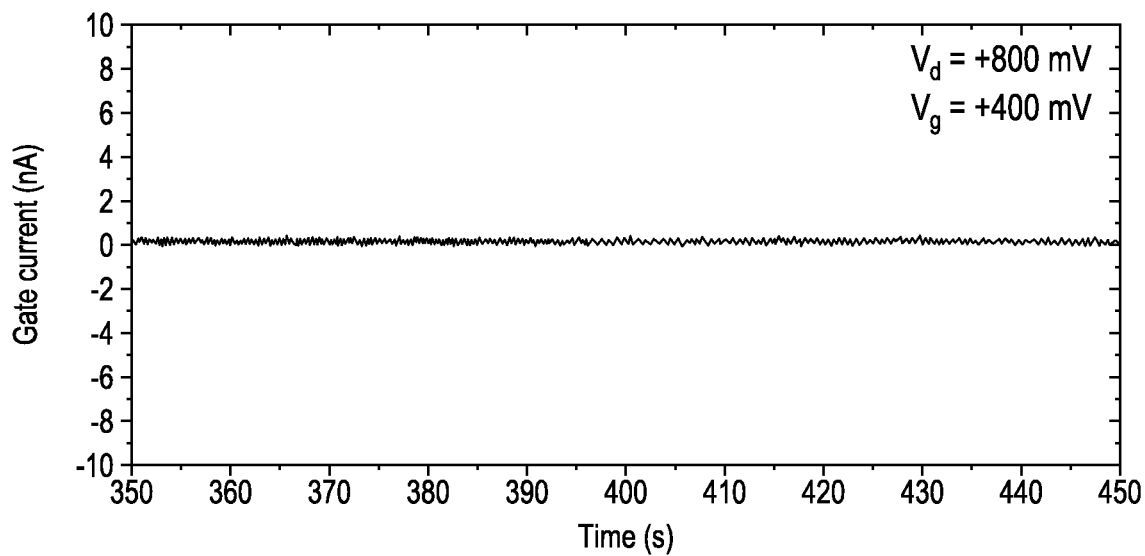
Figure 6I:
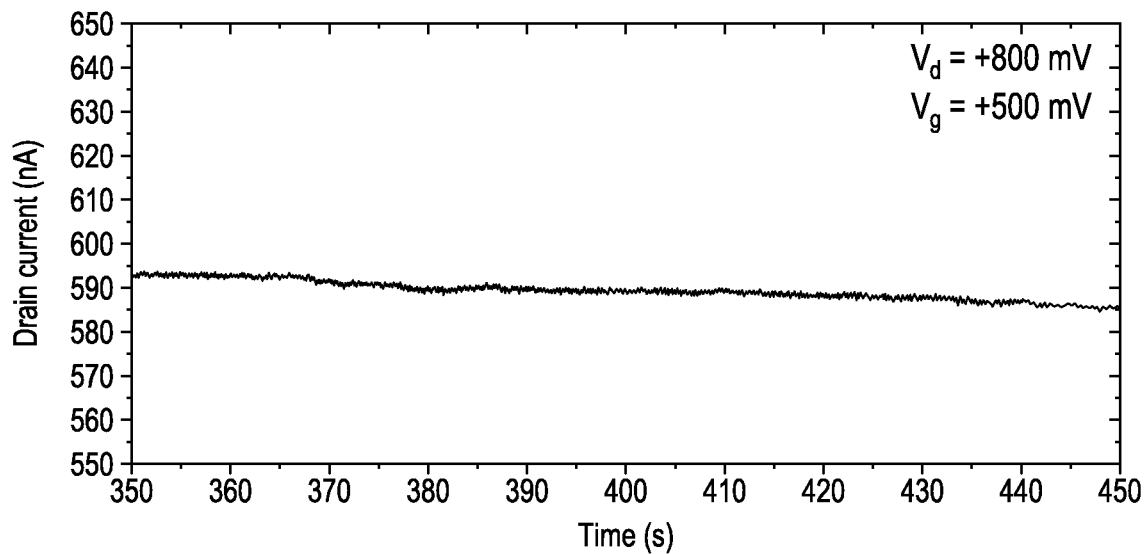
Figure 6J:
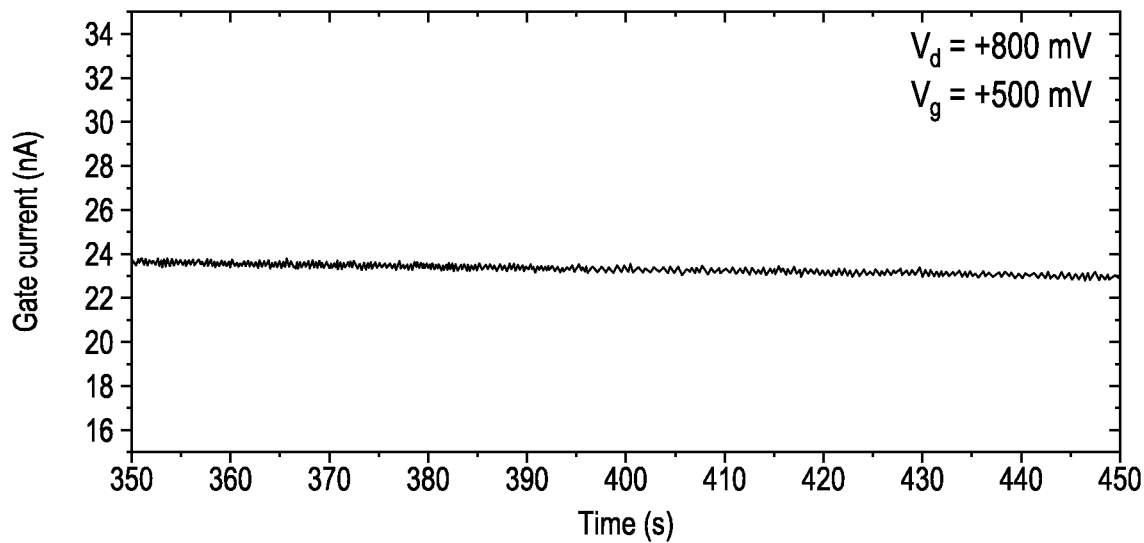

Although a thin layer of $Al_2O_3$ surrounds the gate electrode, the gate can have a small amount of current leak to the source and the drain. FIG. 4A shows an example of gate leakage current ($I_G$) recorded for various NFTs used as a function of the applied gate bias ($V_G$). The choice of $V_G$ range, to ensure low gate leakage current, also keeps the leakage current's effect from dominating the behavior of the NFT. FIG. 4B shows the contribution of the gate leakage to the NFT ionic current by the magnitude ratio of the gate leakage current ($I_G$) to the drain ionic current ($I_D$). The choice of $V_G$ used is near the minima. The time-averaged drain and source ionic currents during the DNA capture rate modulation experiments are shown in FIG. 5. The current-time traces at the drain and the gate electrodes of the thin device are shown in the FIGS. 6A-6J.

In each of the DNA capture rate experiments described herein, $V_D$ was set to +800 to maximize the translocation rates, for the purpose of qPCR analysis, while at the same time keeping the integrity of the devices. It has been experimentally observed that the application of $V_D$=+1 V resulted in very high gate leakage current (>100 nA) which irreversibly damaged the gate electrode.

Detailed numerical simulations have been developed to quantitatively model the device operation, where the electrostatics and the transport of DNAs, cations/anions, and fluids have been fully accounted for. The DNA movement is modeled by the Smoluchowski equation:

$$\nabla \cdot \vec{F}_{DNA} = 0;$$

$$\vec{F}_{DNA} = -D\nabla C_{DNA} + C_{DNA}\mu\nabla\psi + C_{DNA}\vec{u} \quad (2)$$

where $F_{DNA}$ is the DNA flux, $C_{DNA}$ is the DNA concentration, D is the DNA diffusion coefficient, μ is the DNA electrophoretic mobility, ψ is the electrostatic potential, and u is the fluid velocity. The flux is usually dominated by DNA electrophoresis $C_{DNA}\mu\nabla\psi$, and advection, $C_{DNA}\vec{u}$, while diffusion, $-D\nabla C_{DNA}$, plays an insignificant role as demonstrated in these experiments and simulations. Since the external pressures that drive certain embodiments of the present disclosure are negligible, the advection process is determined by the electroosmotic flow (EOF). In the past, the Poisson-Nernst-Plank (PNP) and the Stokes equations were self-consistently solved using a modified version of the general purpose device simulator PROPHET. The solutions to the PNP and Stokes equations are used solve the full Smoluchowski equation for DNA transport.

The solution of Smoluchowski equations, Equation 2, requires the profiles of ψ and u as input. For this purpose, the PNP and Stokes equations are self-consistently solved first for ψ, u, and the concentrations of cations (C+) and anions (C−). The PNP equations are $$\nabla \cdot (\varepsilon_w \nabla \psi) + q(C_+ - C_-) = 0;$$

$$q\nabla \cdot (-D_+ \nabla C_+ - \mu_+ C_+) \nabla \psi + C_- \vec{u}) = 0;$$

$$-q\nabla \cdot (-D_- \nabla C_- + \mu_- C_- \nabla \psi + C_- \vec{u}) = 0 \quad (3)$$

where $\varepsilon_w$ is the dielectric constant of the solution, q the elementary charge, and $D_{+/-}$ and $\mu_{+/-}$ the diffusion coefficients and mobilities of cations and anions, respectively. The fluid transport is modeled by the Stokes divergence equations $$-\nabla p + \gamma \Delta \vec{u} - q(C_+ - C_-) \nabla \psi = 0;$$

$$\nabla \cdot \vec{u} = 0 \quad (4)$$

where p is the solvent pressure and γ is the solvent viscosity.

By analyzing the simulation results, the mechanism of device operation is elucidated. For salt solutions with pH>9.1, the $Al_2O_3$ gate oxide bears a negative surface charge, which makes the direction of DNA electrophoresis and EOF oppose one another. At low $V_G$, the gate enhances $Na^+$ concentration near the pore walls, which results in a strong EOF opposing DNA entry into the pore.

Figure 7:
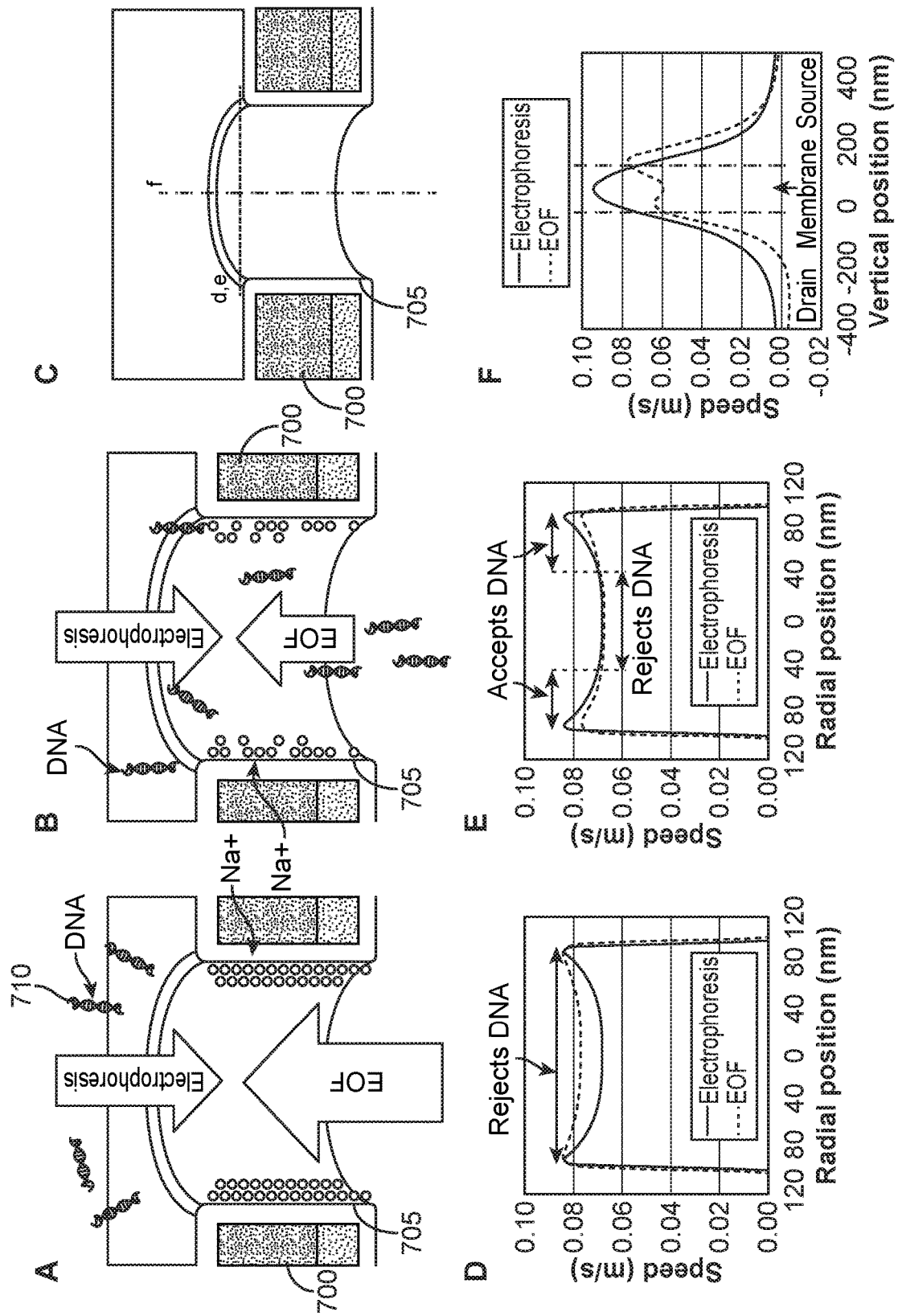
FIG. 7 shows example schematics and corresponding DNA speed plots of as related to electroosmotic flow, consistent with various aspects of the present disclosure.

FIG. 7A illustrates this phenomenon graphically by showing a schematic of the barrier-limited operation when $V_G$ is low. The gate 700 attracts $Na^+$ ions to the pore wall 705. The resulting EOF is stronger than electrophoresis (EP). Despite the strong external electric field acting on the DNA molecules 710, EOF is rejecting DNA 710 from the pore 715, preventing molecular capture. FIG. 7D shows the simulated components of vertical DNA velocities, where at all points along the pore entrance EOF is greater than electrophoresis. At high $V_G$, the electrostatic effect of the gate reduces $Na^+$ concentration near the pore walls. FIG. 7B illustrates the dynamics when $V_G$ is high. The strength of EOF is now lowered below the constant electrophoretic force acting on DNA molecules 710, enabling DNA captured by the pore 715. FIG. 7E shows the plot of simulated components of vertical DNA velocities when $V_G$ is high. Unlike the low $V_G$ case, electrophoretic DNA movement is observed to exceed EOF at the perimeter of the pore 715. The efficient control of DNA capture rate is made possible by operating the NFT in a barrier-limited regime which has previously been studied in detail. Operating the device immediately above or below a certain threshold value of $V_G$, one can obtain exponential (in subthreshold), superlinear (near-threshold), or linear (above-threshold) control over DNA capture rate. Having the EOF much stronger than electrophoresis can reduce the DNA capture exponentially, and having the EOF much weaker than electrophoresis can enhance the DNA capture linearly. Given the choice of pore dimensions, the NFTs operate in subthreshold to near-threshold regime, where a small change in the EOF results in significant modulation of DNA capture rate. FIG. 7F illustrates the electrophoretic DNA speed peaks at the vertical center of the pore. The EOF speed peaks further out the pore 715 in the source side. The difference in the peak locations of EOF and electrophoresis results in a region at the source that rejects DNA from being injected into the pore. FIG. 7C shows the locations where the one-dimensional plots in d, e, and f of FIG. 7 are made.

The EOF profiles in FIGS. 7D and E do not fully develop into the classical profile. EOF was found to take approximately 10 ns to fully develop into its classical profile in a 200 nm wide channel. Since the expected transit time of fluid through the pore is approximately 1 ns, its profile is not fully developed through the short channel. The electric field strength peaks midway through the pore length while EOF peaks near the pore entrance. This shift between the EOF and electrophoresis peaks reveals a region where strong EOF prevents DNA transport across the pore. Further observations about local DNA concentration give insights into the translocation path of DNA molecules.

Figure 8:
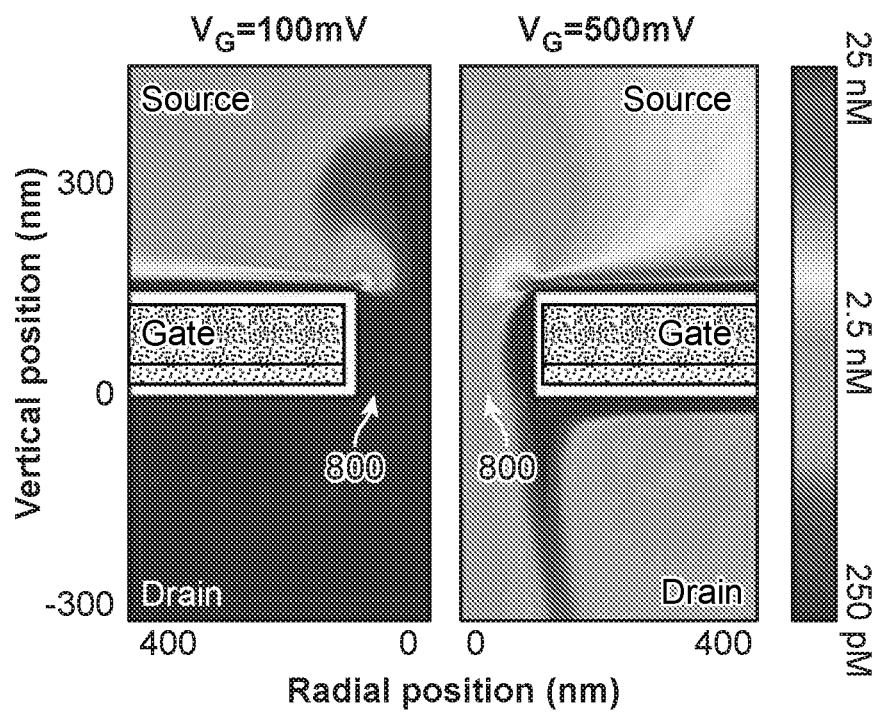
FIG. 8 shows example DNA concentration and driving force due to electroosmotic flow, consistent with various aspects of the present disclosure.
Figure 8:
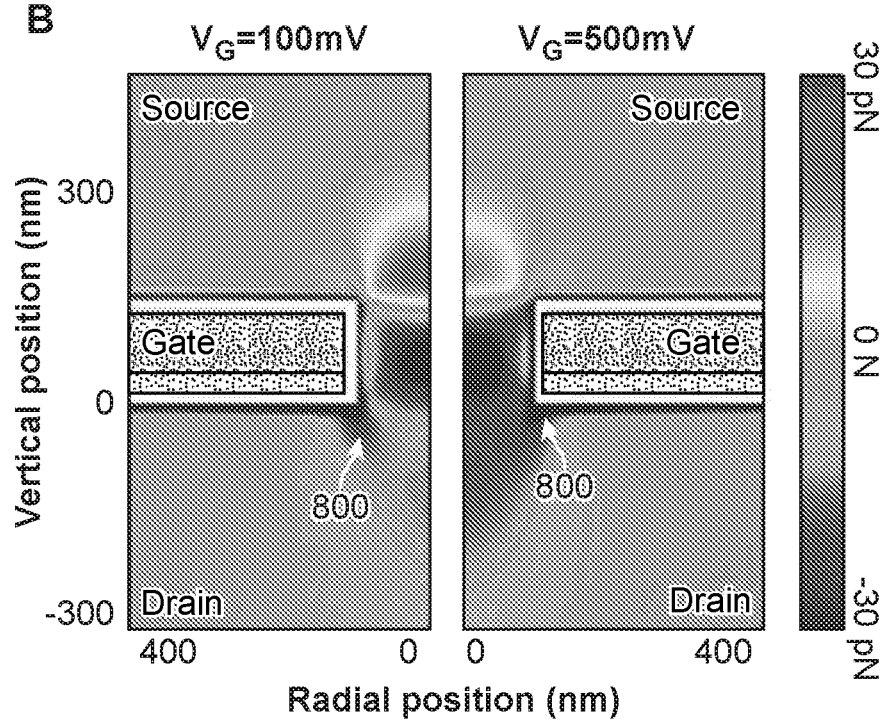

As shown on the left-hand side of FIG. 8A, the strong EOF at low $V_G$ pushes the DNA away from the pore 800 entrance. For the $V_G=+500$ mV case shown on the right-hand side of FIG. 8A, the EOF barrier retreats due to high $V_G$, and the reduced barrier opens the perimeter of the pore 800 to allow DNA to be captured. The shape of the barrier is visualized by looking at the region where DNA is being pushed away from the pore 800, as shown by the driving force plot on the left-hand side of FIG. 8B for the $V_G=+100$ mV case. A plug-shaped barrier is located at the pore entrance and controls the DNA injection into the pore 800. In this case, the device is off, and the plug-shaped barrier fits tightly over the pore 800, severely limiting the capture rate and the translocation velocity. When the device is on, in the $V_G=+500$ mV case on the right-hand side of FIG. 8B, the barrier shrinks in dimension and magnitude and an opening at the perimeter of the pore 800 is created to allow DNA capture. Because the NFT's pore 800 diameter is approximately 200 nm, the translocation kinetics of 100 bp fragments cannot be directly measured by ionic current recording. However, on the basis of the simulation results, the complex dynamics created by the interplay of EOF and electrophoresis, seen in FIG. 8B, may cause a widening of the distribution of translocation speeds. Some DNA molecules will translocate with moderate speeds, while others will be held near the border between the barrier and the opening seen in FIG. 8B. This also results in the local DNA concentration enhancements near the entrance of the pore seen in FIG. 8A.

The threshold behavior observed in NFTs in various embodiments of the present disclosure can enable the selective capture of biomolecules based on their free-solution electrophoretic mobility or by the use of drag tags. According to Equation 2, and the fact that the diffusion only plays a negligible role, the capture of biomolecules by the NFTs is primarily mobility-dependent. Such a characteristic can be used to purify biomolecules in lab-on-a-chip devices.

By adjusting the NFT's dimensions, its surface property, the salt concentration, and the pH, the interplay between the EOF and DNA electrophoresis is varied. As revealed by detailed numerical simulations, the counter-balance of these opposing flows is a contributing factor to the operation of NFT devices of the present disclosure. The resultant barrier-limited operation enables NFTs, consistent with various aspects of the present disclosure, to control the rate of capture of DNA by at least 3 orders of magnitude with a sub-1 V bias applied to an embedded metal gate. Further, the solution pH, in certain embodiments, tunes the threshold voltage.

Figure 9:
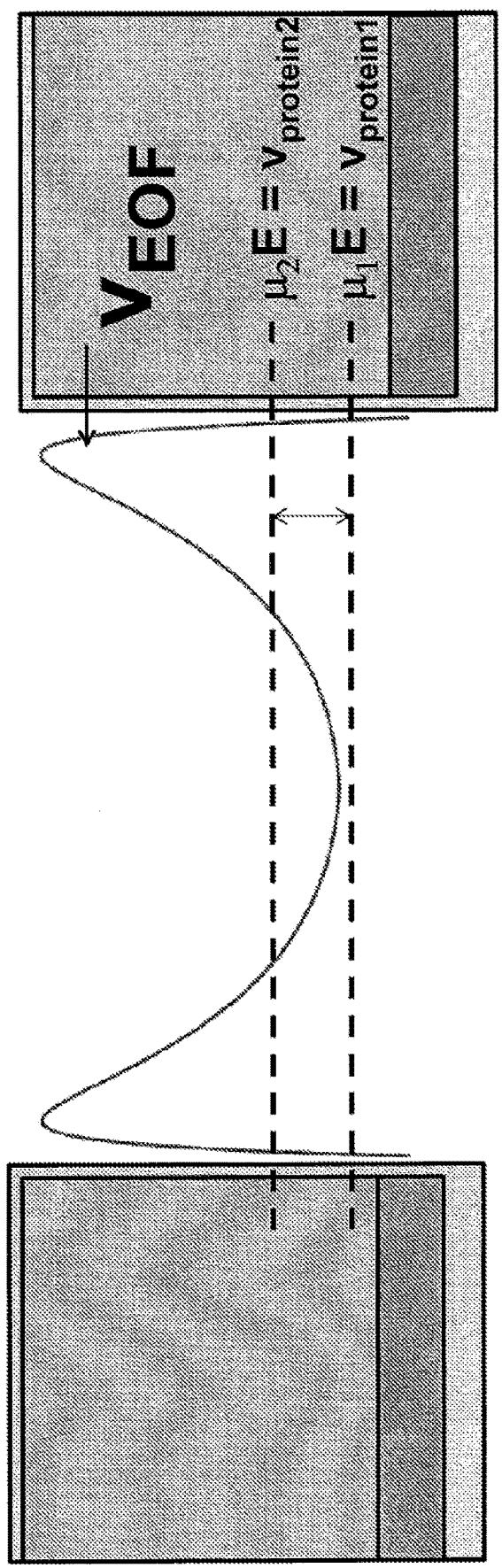
FIG. 9 shows an example schematic of an NFT apparatus compared to two speed plots of proteins as related to electroosmotic flow, consistent with various aspects of the present disclosure.

FIG. 9 shows an example schematic of an NFT apparatus compared to two speed plots of proteins as related to electroosmotic flow, consistent with various aspects of the present disclosure. As shown therein, an external electric field (E) drives biomolecules such as proteins through the pore. FIG. 9 displays two proteins that have differing motilities. Electroosmotic flow opposes the velocity of the proteins, such that the mobility of the counterion ($\mu$) multiplied by the electric field must be greater than the electroosmotic forces in order for the biomolecule to pass through the pore. As shown in FIG. 9, the second protein satisfies this condition, whereas the first protein does not satisfy the condition for passage.

Figure 10:
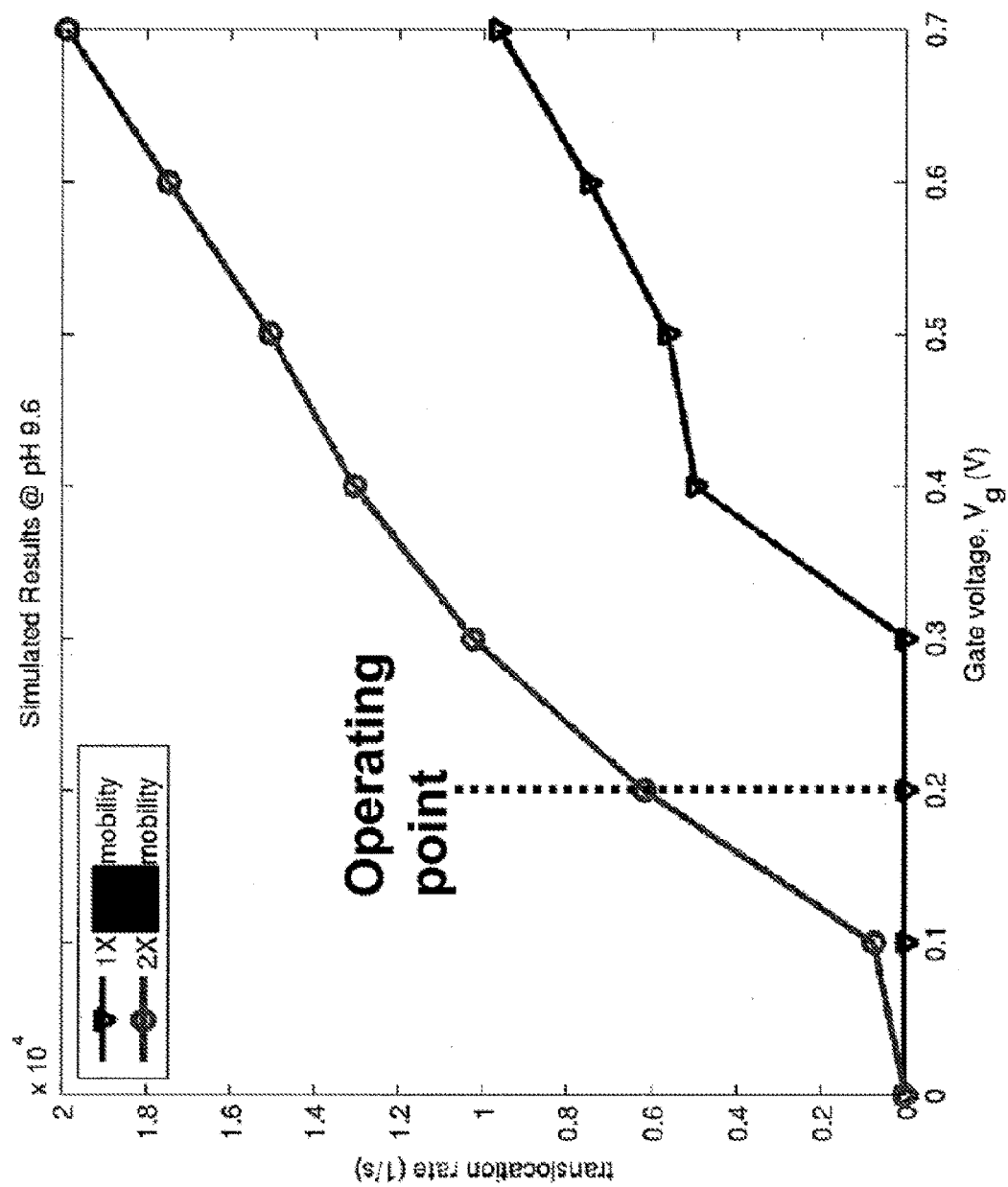
FIG. 10 shows an example capture rate simulation of two different biomolecules using an NFT apparatus, consistent with various aspects of the present disclosure.

FIG. 10 shows an example capture rate simulation of two different biomolecules using an NFT apparatus, consistent with various aspects of the present disclosure. As shown in FIG. 10, by operating the device at the operating point, the more mobile of the two biomolecules are collected while rejecting the capture of the less mobile biomolecules.

Figure 11A:
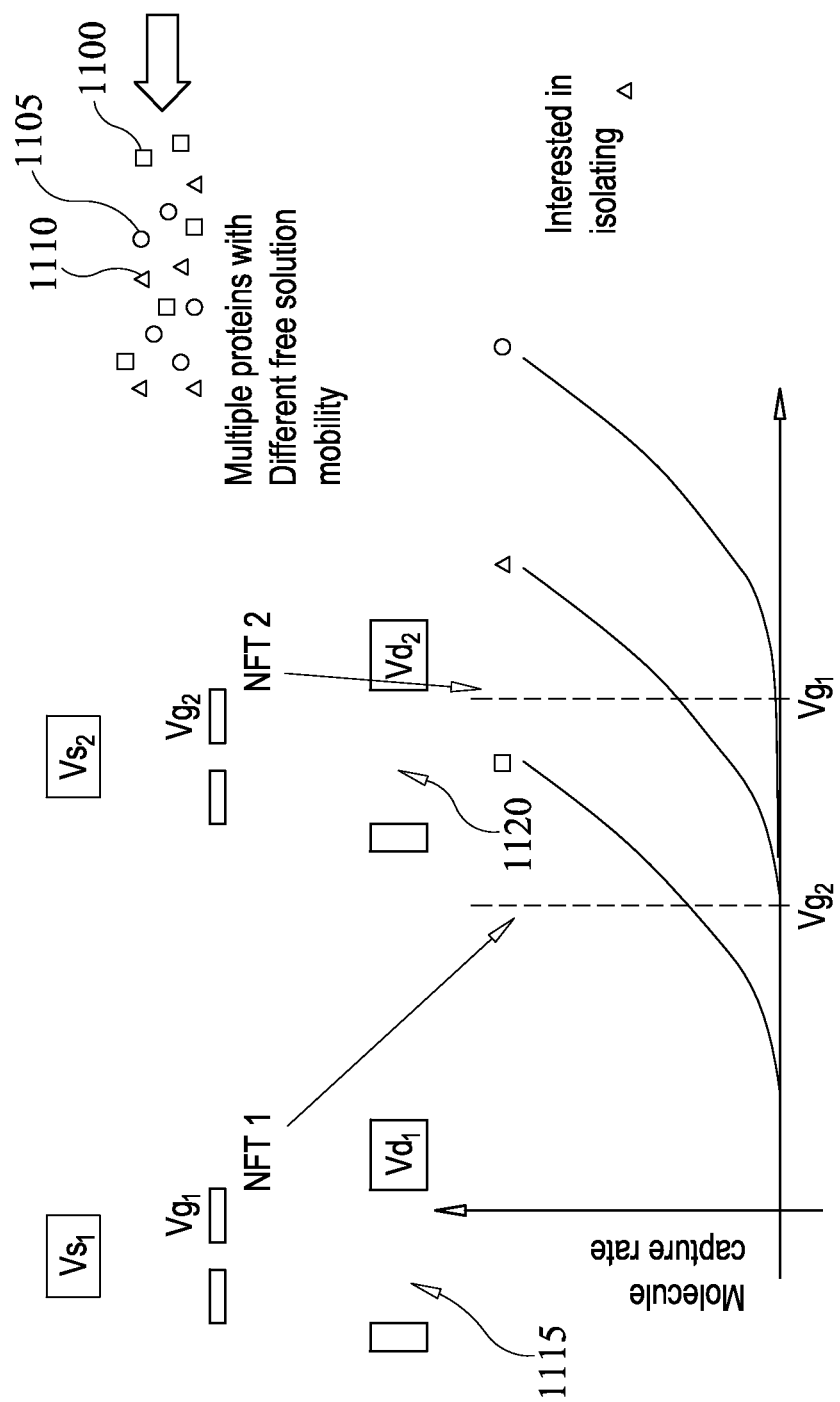
FIG. 11A-11D show example protein purification models using an NFT apparatus, consistent with various aspects of the present disclosure.
Figure 11B:
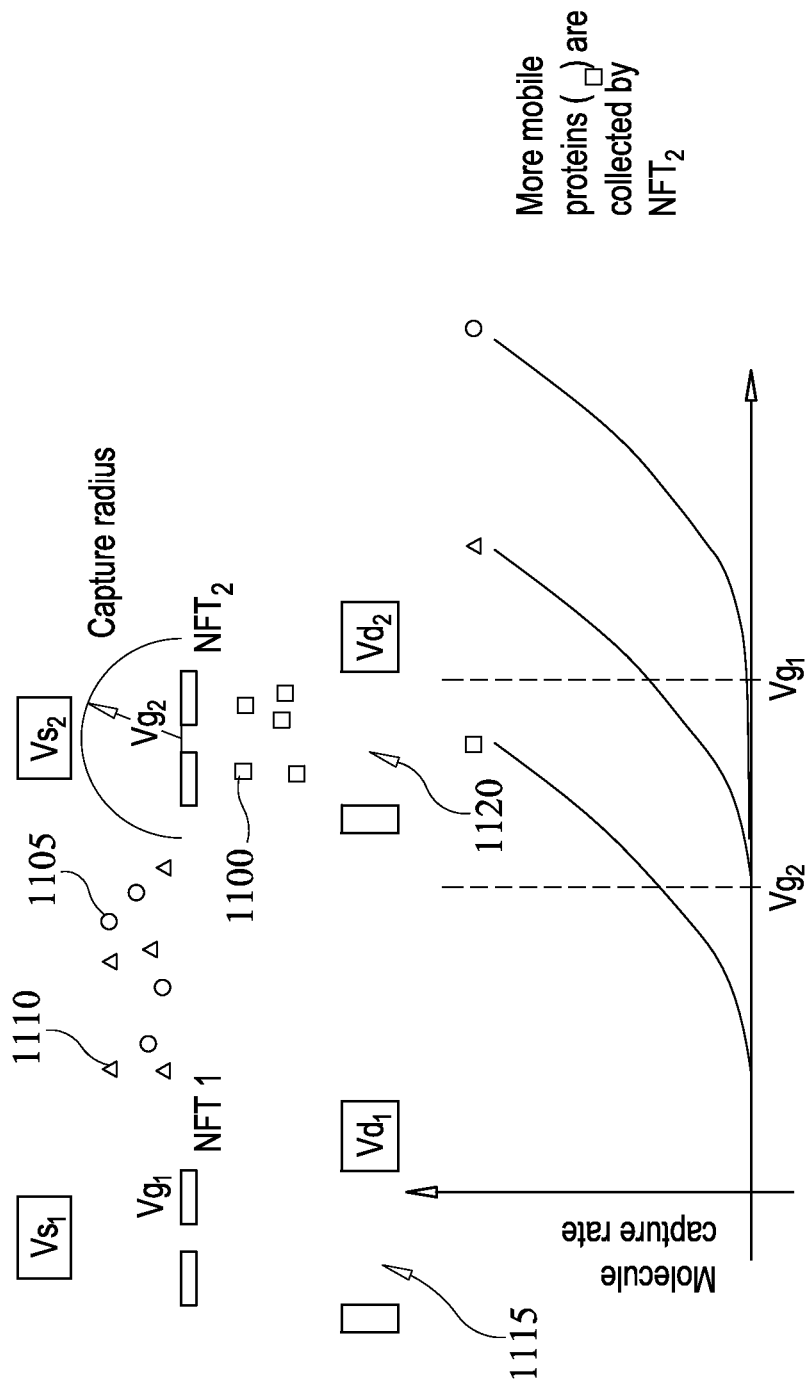
Figure 11C:
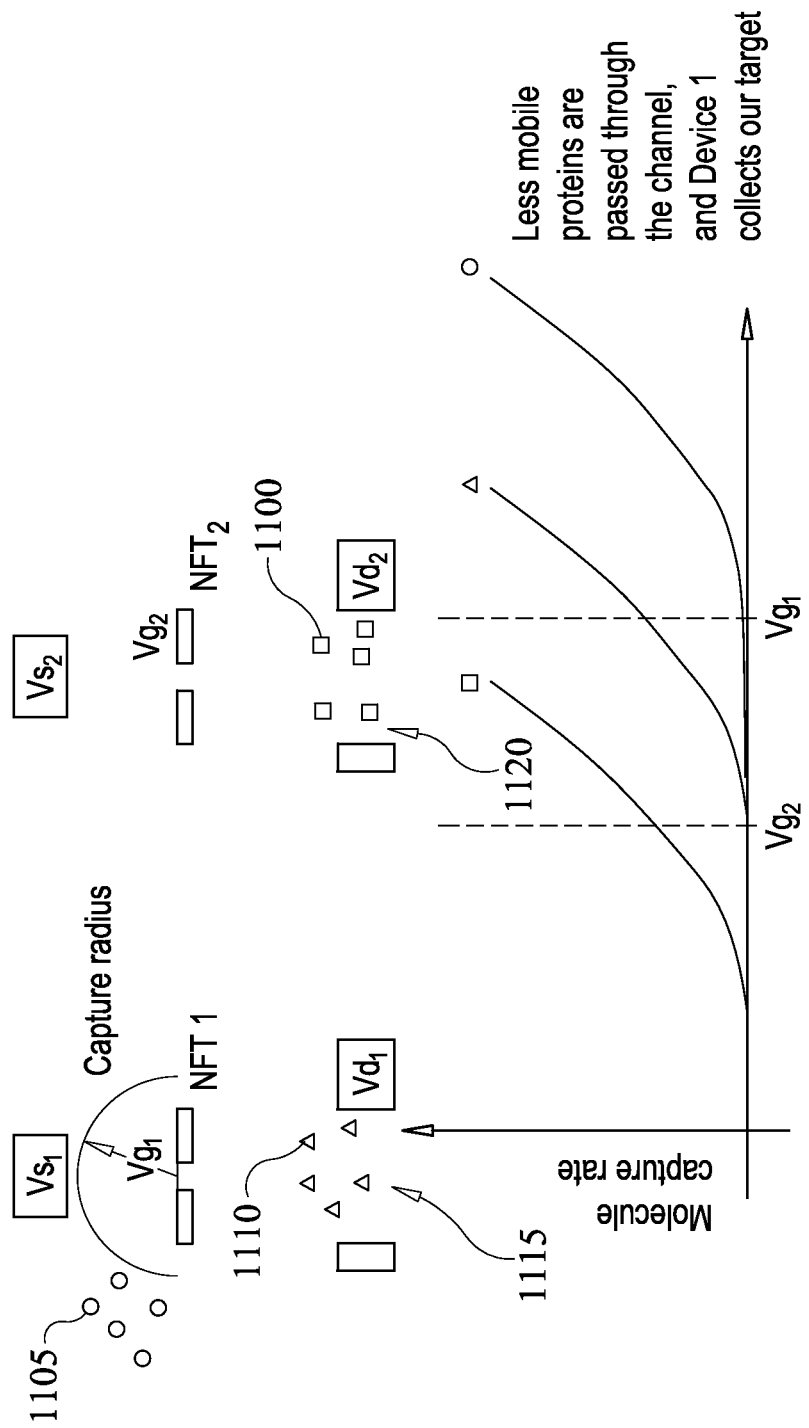
Figure 11D:
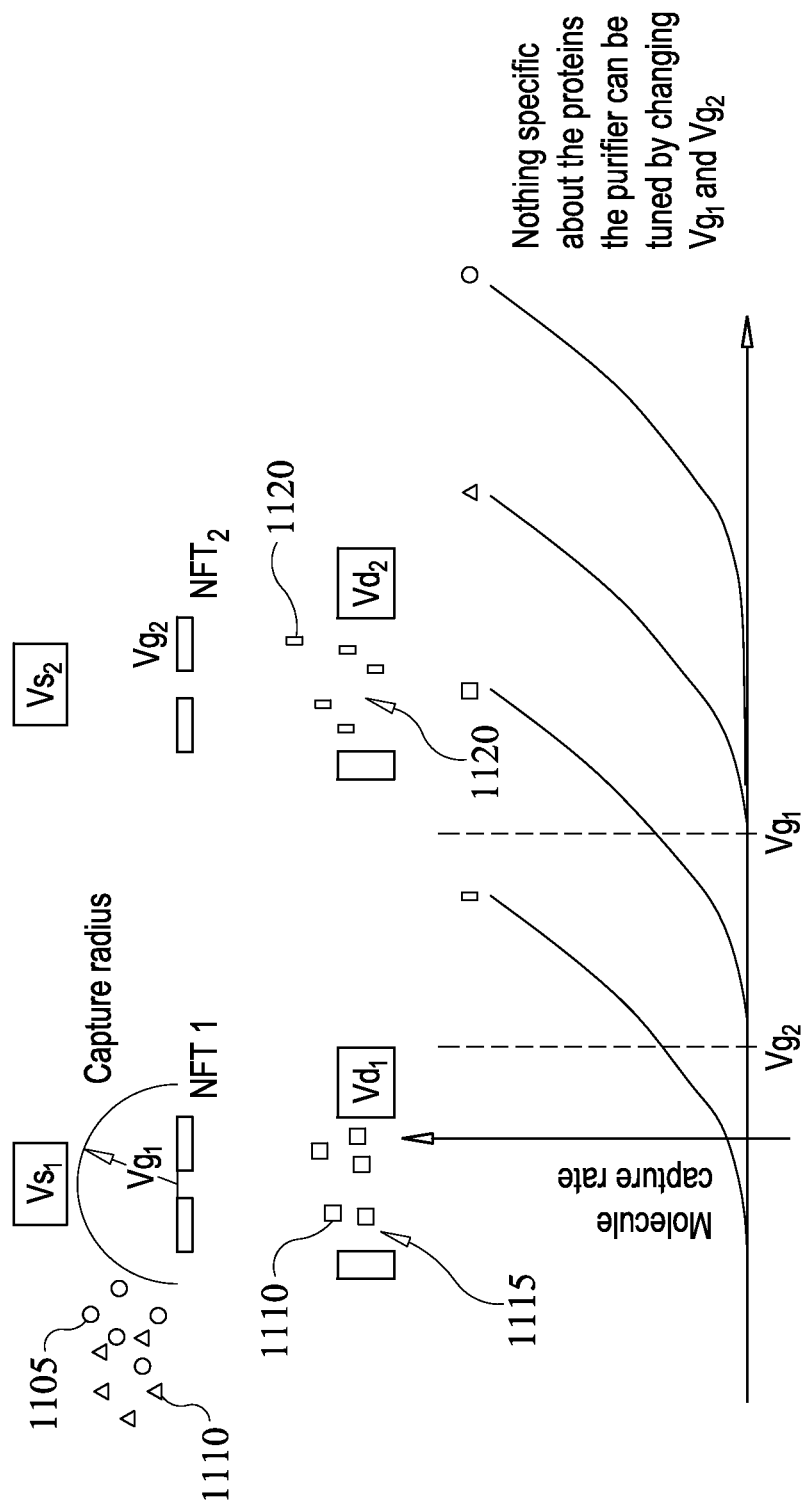

FIGS. 11A-11D show example protein purification models using NFT apparatuses, consistent with various aspects of the present disclosure. Two NFT apparatuses (NFT 1 and NFT 2) are shown in FIGS. 11A-11D, each having a source voltage ($V_s$), a gate voltage ($V_g$), and a drain voltage ($V_d$). Multiple proteins (1100, 1105, 1110, 1125) with different free solution mobility are represented by different shapes in each of FIGS. 11A-D. As shown in FIG. 11A, the different proteins (1100, 1105, 1110) flow towards the first 1115 and second pores 1120 in the NFT apparatuses. As discussed in detail above, based on the differing voltages applied to the NFT apparatuses (as shown in the bottom portions of FIGS. 11A-D), proteins having different nobilities can be captured. The second NFT apparatus (NFT 2), shown in FIG. 11B, collects the more mobile proteins (1100). The capture radius of the second NFT apparatus (NFT 2) spans the channel near and around the second NFT apparatus (NFT 2). As shown in FIG. 11C, the less mobile proteins (and targeted proteins) (1105 and 1115) evade capture by the second NFT apparatus (NFT 2), and are captured by the first NFT apparatus (NFT 1). The capture radius of the first NFT apparatus (NFT 1) spans the channel near and around the first NFT apparatus (NFT 1). As shown in FIG. 11D, different proteins (1100, 1105, 1110) can be captured by each of the NFT apparatuses by tuning the gate voltages of the NFT apparatuses.

Figure 12:
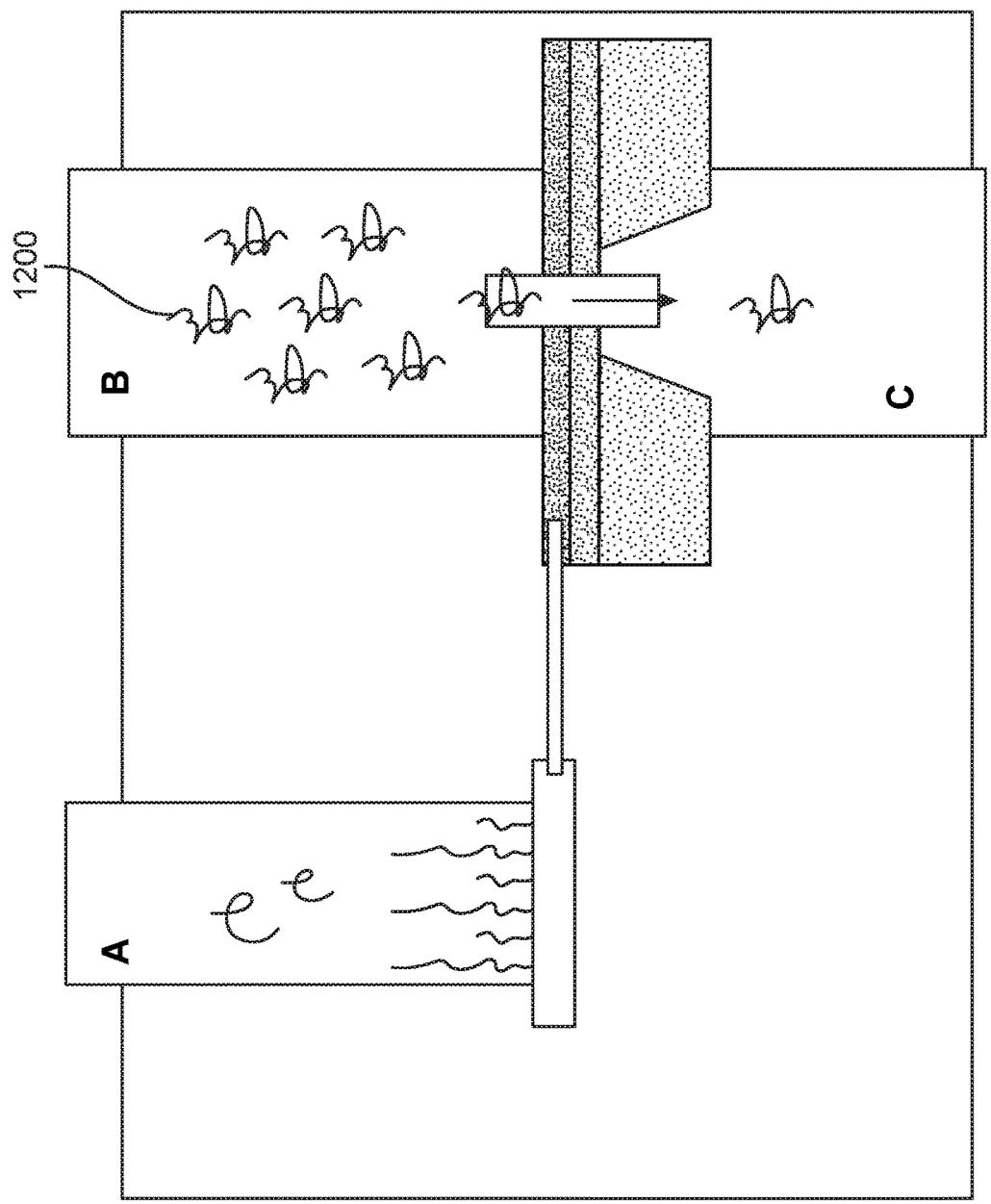
FIG. 12 shows an example bio-molecule valve/amplifier, consistent with various aspects of the present disclosure.

FIG. 12 shows an example bio-molecule valve/amplifier, consistent with various aspects of the present disclosure. As shown therein, triggering molecules (A) are concentrated in a first chamber. Controlled concentration of molecules 1200 in well C occurs by modulating passage of the molecules from reservoir B, in accordance with the description above.

Figure 13:
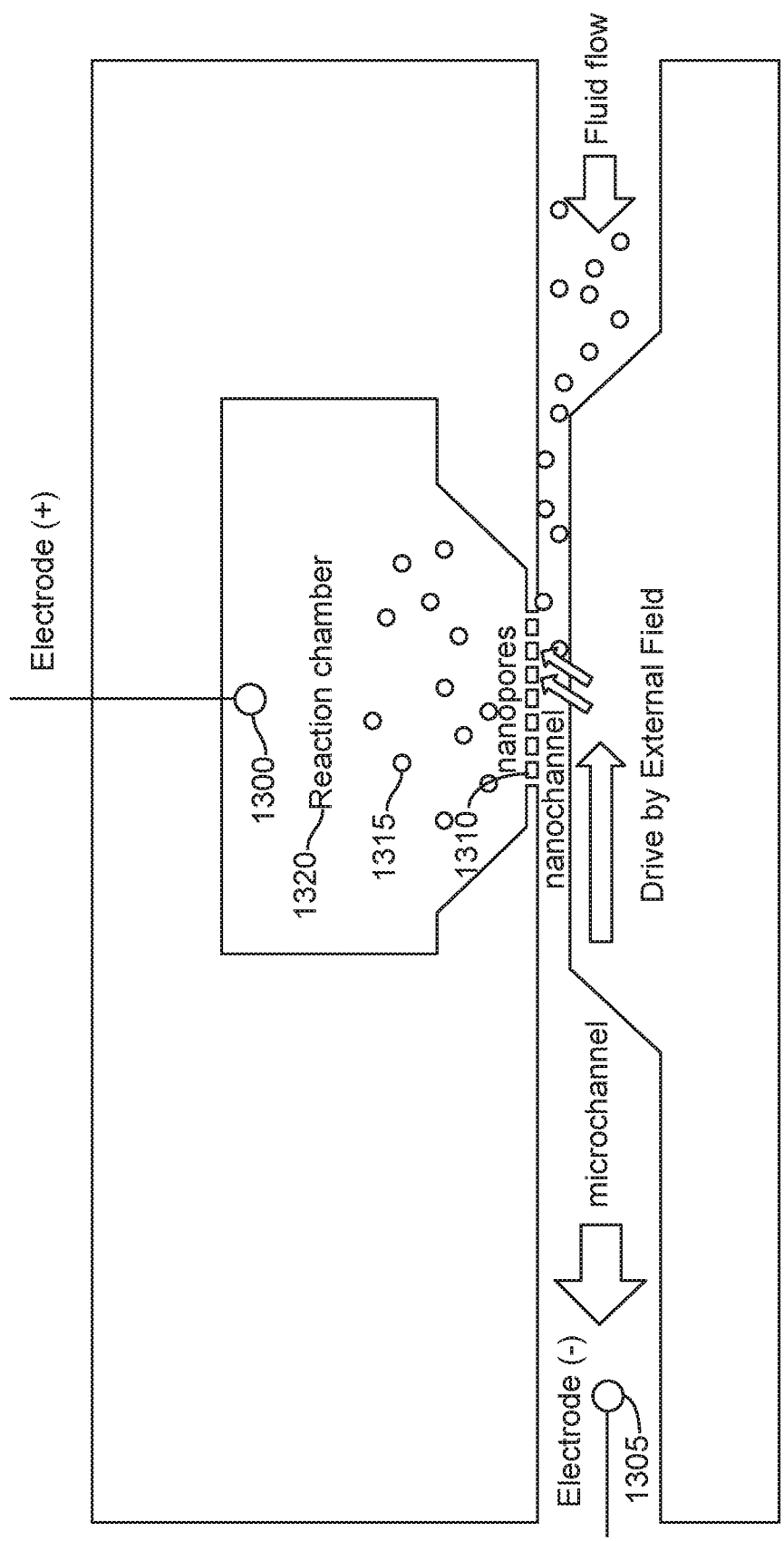
FIG. 13 shows an example schematic of device and method for pre-concentration of biomolecules, consistent with various aspects of the present disclosure.

FIG. 13 shows an example schematic of device and method for pre-concentration of biomolecules, consistent with various aspects of the present disclosure. A voltage is applied to the electrodes 1300/1305 such that the pores 1310 capture DNA molecules 1315 and the electric field in the channel keeps the DNA molecules 1315 near the nanopores 1310 for more efficient capture. Combining pressure driven microfluidic devices and an electrophoretic nanofluidic device, consistent with various aspects of the present disclosure, the device is capable of collecting, for example, cell free DNA, often short (500 bp) fragments of DNA, and analyzing them with an integrated fluidic device. A body of fluid containing small amounts of cell free DNA is pressure driven across the device. The device shown in FIG. 13 confines the electric field creating an environment that will not only attract DNA molecules 1315 into a reaction chamber 1320 but also make it un-favorable for DNA to flow across the device without being collected into the reaction chamber 1320. With sufficiently high field applied, the reaction chamber is able to collect nearly all DNA molecules. Once the DNA molecules 1315 are in the reaction chamber, an integrated detection method can be used to analyze the content of the chamber.

For further discussion of electrostatic control of a capturing of biomolecules, as relating to the embodiments and specific applications discussed herein, reference may be made to the underlying U.S. Provisional Patent Application, Ser. No. 61/708,510 filed on Oct. 1, 2012 (including the Appendices therein) to which priority is claimed and which are fully incorporated herein by reference generally and for the reasons noted above. The aspects discussed therein may be implemented in connection with one or more of embodiments and implementations of the present disclosure (as well as with those shown in the figures). Moreover, for general information and for specifics regarding applications and implementations to which one or more embodiments of the present disclosure may be directed to and/or applicable, reference may be made to the references cited in the aforesaid patent application and published article, which are fully incorporated herein by reference generally and for the reasons noted above. In view of the description herein, those skilled in the art will recognize that many changes may be made thereto without departing from the spirit and scope of the present disclosure.

Based upon the above discussion and illustrations, those skilled in the art will readily recognize that various modifications and changes may be made without strictly following the exemplary embodiments and applications illustrated and described herein. Furthermore, various features of the different embodiments may be implemented in various combinations. Such modifications do not depart from the true spirit and scope of the present disclosure, including those set forth in the following claims.

What is claimed is:

1. An apparatus comprising:
a membrane having at least one fluidic pore extending between opposing surfaces of the membrane; and
first and second electrodes arranged on opposite sides of the fluidic pore of the membrane,
wherein the membrane includes:
(a) a third electrode having at least one pore extending between opposite sides of the third electrode; and
(b) an insulator layer disposed on the opposite sides of the third electrode and extending through the pore of the third electrode, the insulator layer has a homogeneous material composition, the fluidic pore of the membrane extends through the pore of the third electrode, and the insulator layer fully defines a sidewall of the fluidic pore of the membrane.

2. The apparatus of claim 1, further including a first reservoir and a second reservoir arranged on opposite sides of the fluidic pore of the membrane.

3. The apparatus of claim 1, further including a sensor adjacent to and outside of the fluidic pore of the membrane.

4. The apparatus of claim 3, further including a signal processing circuit connected to the sensor.

5. An apparatus comprising:
a membrane having at least one fluidic pore extending between opposing surfaces of the membrane; and
source and drain electrodes arranged on opposite sides of the fluidic pore of the membrane,
wherein the membrane includes:
(a) a gate electrode having at least one pore extending between opposite sides of the gate electrode; and
(b) an insulator layer disposed on the opposite sides of the gate electrode and extending through the pore of the gate electrode, the insulator layer has a homogeneous material composition, the fluidic pore of the membrane extends through the pore of the gate electrode, and the insulator layer fully defines a sidewall of the fluidic pore of the membrane.

6. The apparatus of claim 5, further including a sensor adjacent to and outside of the fluidic pore of the membrane.

7. A method comprising:
providing a membrane having at least one fluidic pore extending between opposing surfaces of the membrane;
using first and second electrodes to facilitate movement of analytes in a fluid through the fluidic pore of the membrane; and
applying a bias to a third electrode included in the membrane and adjacent to the fluidic pore of the membrane to control the movement of the analytes, thereby modulating the shape of an electric double layer adjacent a sidewall of the fluidic pore of the membrane and within the fluidic pore of the membrane and thereby controlling the strength of an electroosmotic fluid flow that opposes said movement of the analytes via the fluidic pore of the membrane,
wherein the third electrode has at least one pore extending between opposite sides of the third electrode, the membrane further includes an insulator layer disposed on the opposite sides of the third electrode and extending through the pore of the third electrode, the insulator layer has a homogeneous material composition, the fluidic pore of the membrane extends through the pore of the third electrode, and the insulator layer fully defines the sidewall of the fluidic pore of the membrane.

8. The method of claim 7, wherein using the first and second electrodes to facilitate movement of the analytes through the fluidic pore of the membrane includes using the first and second electrodes to electrophoretically flow the analytes through the fluidic pore of the membrane, further including providing and accepting the analytes for electrophoresis thereof via reservoirs on opposite sides of the fluidic pore of the membrane.

9. The method of claim 7, further including sensing a characteristic of the analytes in the fluidic pore of the membrane.

10. The method of claim 7, wherein the bias applied at the fluidic pore of the membrane is below 1 V.

11. The apparatus of claim 1, wherein the insulator layer fully covers the third electrode adjacent to the sidewall of the fluidic pore of the membrane.

12. The apparatus of claim 5, wherein the insulator layer fully covers the gate electrode adjacent to the sidewall of the fluidic pore of the membrane.

* * * * *